US009678082B2

(12) United States Patent
Lin et al.

(10) Patent No.: US 9,678,082 B2
(45) Date of Patent: Jun. 13, 2017

(54) METHOD OF TRACELESS LABELING GLYCOPROTEINS ON SURFACE AND APPLICATION THEREOF

(71) Applicant: NATIONAL SUN YAT-SEN UNIVERSITY, Kaohsiung (TW)

(72) Inventors: Po-Chiao Lin, Kaohsiung (TW); Yung-Lin Yang, Tainan (TW); Yen-Pin Lee, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 483 days.

(21) Appl. No.: 14/529,178

(22) Filed: Oct. 31, 2014

(65) Prior Publication Data

US 2016/0123988 A1 May 5, 2016

(51) Int. Cl.
G01N 33/68 (2006.01)
G01N 33/543 (2006.01)
G01N 33/551 (2006.01)

(52) U.S. Cl.
CPC ... *G01N 33/6842* (2013.01); *G01N 33/54306* (2013.01); *G01N 33/54353* (2013.01); *G01N 2400/00* (2013.01)

(58) Field of Classification Search
CPC ......... G01N 33/6842; G01N 33/54306; G01N 33/54353; G01N 2400/00
See application file for complete search history.

(56) References Cited

PUBLICATIONS

Isaac S. Carrico, Chemoselective modification of proteins: hitting the target, Chemical Society Reviews, Jun. 5, 2008, 37, pp. 1423-1431.

Roger Y. Tsien, The Green Fluorescent Protein, Annu. Rev. Biochem., 1998, 67:509-544.
Emmanuel Basle et al., Protein Chemical Modification on Endogenous Amino Acids, Chemistry & Biology, Mar. 26, 2010, 17:213-227.
Marlon J Hinner and Kai Johnsson, How to obtain labeled proteins and what to do with them, Chemical biotechnology, Oct. 26, 2010, 21:766-776.
TaeWoon Cha et al., Enzymatic activity on a chip: The critical role of protein orientation, Proteomics 2005, 5:416-419.
Po-Chiao Lin et al., Site-Specific Protein Modification through Cui-Catalyzed 1,2,3-Triazole Formation and Its Implementation in Protein Microarray Fabrication, Angew. Chem. Int. Ed., May 31, 2006, 45: 4286-4290.
Sletten, E. M., and Bertozzi, C. R., Bioorthogonal chemistry: fishing for selectivity in a sea of functionality, Angew Chem Int Ed Engl., 2009, 48(38): 6974-6998.

(Continued)

*Primary Examiner* — Jeremy C Flinders
(74) *Attorney, Agent, or Firm* — CKC & Partners Co., Ltd.

(57) ABSTRACT

The present invention relates to a method of traceless labeling glycoproteins on a surface and an application thereof. A test glycoprotein can be immobilized on a surface using a BA-tosyl probe and the BA-tosyl probe is then released using a releasing agent, so as to expose a glycan residue of the test glycoprotein. The exposed glycan residue of the test glycoprotein can be detected without altering native glycan structures. Moreover, the present invention further provides a detection kit of traceless labeling glycoproteins on a surface in the study of glycoprotein-protein interactions, which is suitable for using the aforementioned method.

23 Claims, 12 Drawing Sheets

(56) References Cited

PUBLICATIONS

Lim, R. K., and Lin, Q., Bioorthogonal chemistry: recent progress and future directions, Chem Commun (Camb), Mar. 14, 2010, 46(10): 1589-1600.

Saxon, E., and Bertozzi, C. R., Cell surface engineering by a modified Staudinger reaction, Science, Mar. 17, 2000, 287:2007-2010.

Wang, L., Brock, A., Herberich, B., and Schultz, P. G., Expanding the genetic code of *Escherichia coli*, Science, Apr. 29, 2001, 292: 498-500.

Adam, G. C., Sorensen, E. J., and Cravatt, B. F., Proteomic profiling of mechanistically distinct enzyme classes using a common chemotype, Nat. Biotechnol., Aug. 2002, 20: 805-809.

Barglow, K. T., and Cravatt, B. F., Activity-based protein profiling for the functional annotation of enzymes, Nat. Methods, Sep. 27, 2007, 4: 822-827.

Adam, G. C., Cravatt, B. F., and Sorensen, E. J., Profiling the specific reactivity of the proteome with non-directed activity-based probes, Chem. Biol., 2001, 8:81-95.

Hamachi, I., Nagase, T., and Shinkai, S., A general semisynthetic method for fluorescent saccharide-biosensors based on a lectin, J. Am. Chem. Soc., Nov. 17, 2000, 122: 12065-12066.

Fujishima, S. H., Yasui, R., Miki, T., Ojida, A., and Hamachi, I., Ligand-directed acyl imidazole chemistry for labeling of membrane-bound proteins on live cells, J. Am. Chem. Soc., Feb. 21, 2012, 134:3961-3964.

Koshi, Y., Nakata, E., Miyagawa, M., Tsukiji, S., Ogawa, T., and Hamachi, I., Target-specific chemical acylation of lectins by ligand-tethered DMAP catalysts, J. Am. Chem. Soc., 2008, 130: 245-251.

Takaoka, Y., Tsutsumi, H., Kasagi, N., Nakata, E., and Hamachi, I., One-pot and sequential organic chemistry on an enzyme surface to tether a fluorescent probe at the proximity of the active site with restoring enzyme activity, J. Am. Chem. Soc., Feb. 21, 2006, 128: 3273-3280.

Hayashi, T., and Hamachi, I., Traceless affinity labeling of endogenous proteins for functional analysis in living cells, Acc. Chem. Res., Jun. 8, 2012, 45: 1460-1469.

Tsukiji, S., Miyagawa, M., Takaoka, Y., Tamura, T., and Hamachi, I., Ligand-directed tosyl chemistry for protein labeling in vivo, Nat. Chem. Biol., May 2009, 5:341-343.

Tsukiji, S., Wang, H., Miyagawa, M., Tamura, T., Takaoka, Y., and Hamachi, I., Quenched ligand-directed tosylate reagents for one-step construction of turn-on fluorescent biosensors, J. Am. Chem. Soc., Jun. 5, 2009, 131:9046-9054.

Tamura, T., Tsukiji, S., and Hamachi, I., Native FKBP12 engineering by ligand-directed tosyl chemistry: labeling properties and application to photo-cross-linking of protein complexes in vitro and in living cells, J. Am. Chem. Soc., 2012, 134: 2216-2226.

Varki, A., Biological roles of oligosaccharides: all of the theories are correct, Glycobiology, 1993, 3:97-130.

METHOD OF TRACELESS LABELING GLYCOPROTEINS ON SURFACE AND APPLICATION THEREOF

BACKGROUND

Field of Invention

The present invention relates to a method of labeling glycoproteins on a surface and an application thereof producing the same. More particularly, the present invention relates to a method of traceless labeling glycoproteins on the solid surface without altering the composition of mono/oligo-saccharides and an application thereof.

Description of Related Art

The use of synthetic molecules to label and track proteins of interest accelerates progress in the studies of protein function, localization, and structure, which are closely related to biological significance. Synthetic chemistry is a central component of modern chemical biology, providing tailored molecules that can be used for the precise, covalent modification of biomolecules of interest. Compared to protein fusion-based methods using green fluorescent protein or affinity protein tags, the chemistry-oriented strategy with small organic probes better conserves the native structures of target proteins and reduces their loss of biological activity. Therefore, the development of chemical methods of protein labeling can certainly reduce the undesired alteration of important tertiary structures of the protein. The techniques can be used in studies of protein-ligand, protein-protein, and protein-biomolecule interactions and are especially suitable in complex biological environments.

However, with conventional chemical methods for protein labeling, such as the formation of an amide bond, Schiff base, or other covalent conjugations, lack of regioselectivity and multiple reaction sites are always observed between probe molecules and the endogenous residues of proteins, therefore leading to ambiguous results. Accordingly, a substantial improvement of the chemical probes used in the site-selective modification of target proteins must be accompanied by a combination of bioorthogonal chemistry and metabolically or genetically incorporated chemical entities. However, the use of molecular biology techniques such as the incorporation of noncanonical amino acids or genetic engineering for advanced bioorthogonal conjugation may induce to a change in protein activity. Thus, a need is emerging for a new method for the site-selective labeling of endogenous proteins in their native habitats. To this end, some researchers proposed a method termed 'activity-based protein profiling' (ABPP), which allows the characterization of several enzymes in their active states through protein activity-directed recognition. Proteins of interest can be selectively labeled and isolated by this method; however, the chemical probes may inactivate the labeled proteins.

It is believed that more than 50% of known proteins are subject to post-translational glycosylation, and the glycosylation process plays a key role in the recognition events involved in cell development, immunology, and cancer biology. Glycosylation in protein modification refers to the covalent attachment of a diverse set of one or more sugar molecules to a protein; the sugar part of the glycoproteins thus formed is termed a "glycan". Certainly, glycoproteins are involved in many important biological processes; however, only a few glycan-based targeting strategies are currently available, and most of them result in an irreversible alteration of native glycan structures. The structural alteration of a glycan always results in a considerable loss of its biological significance.

There is, however, a growing need for new methods of glycoprotein labeling and enrichment is emerging, for overcoming all issues of conventional glycoprotein labeling methods and accelerating the understanding of glycoproteins and their role in the advanced regulation of the cell life cycle.

SUMMARY

The invention provides a method of traceless labeling glycoproteins on a surface, in which the on-surface boronic acid (BA)-tosyl probe can bring a test glycoprotein immobilized on a surface and finally expose the native glycan residues of the test glycoprotein, so as to detecting the glycan residue of the test glycoprotein without altering native glycan structures.

Moreover, the present invention provides a detection kit of traceless labeling glycoproteins on a surface, in which the detection kit is suitable for being applied in the aforementioned method.

Accordingly, the invention provides a method of traceless labeling glycoproteins on a surface. Firstly, a solid surface is provided, in which the solid surface has activated ester groups coated thereon. Next, the activated ester groups on the solid surface reacts with an amino linker, such that a terminal amine group of the amino linker is covalently bound to a part of the activated ester groups and a terminal azide group of the amino linker is exposed. In this embodiment, the amino linker has a structure listed as formula (I):

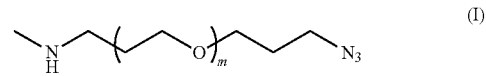

in the formula (I), the m represents an integer of 1 to 3.

And then, unreacted parts of the activated ester groups are blocked by a first blocking agent. In an embodiment, the other part of the activated ester groups are unreacted with the terminal amine group of the amino linker, and the first blocking agent is a glycol solution. Later, the terminal azide group reacts with a terminal alkyne group of a boric acid (BA)-tosyl probe, such that the BA-tosyl probe is immobilized on the surface via a first covalent bond and a BA moiety of the BA-tosyl probe is exposed. In an embodiment, the BA-tosyl probe has a structure listed as formula (II):

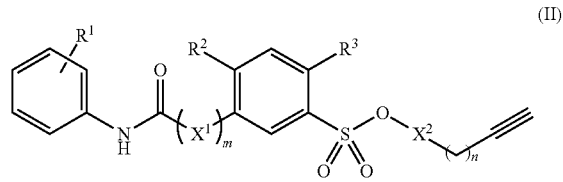

in the formula (II), the $R^1$ is a boron-containing group, and an aromatic group having the $R^1$ group in the formula (II) represents a structure listed as formulas (III) to (V); the $R^2$ is a hydrogen atom, a halide atom or an alkyl group having 1 to 3 carbon numbers; the $R^3$ is a hydrogen atom or a halide atom; the $X^1$ represents —$R^4_a R^5$—, the $X^2$ represents —$R^6_p R^7_q$—, the $R^4$ has a structure listed as formula (VI), the $R^5$ has a structure listed as formula (VII), the $R^8$ has a structure listed as formula (VIII), the $R^7$ has a structure listed as formula (IX), the m represents an integer of 0 or 1, the n represents an integer of 1 to 12, and the a, p or q independently and individually represents an integer of 0 or 1;

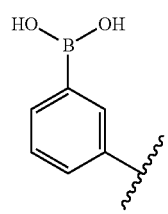(III)

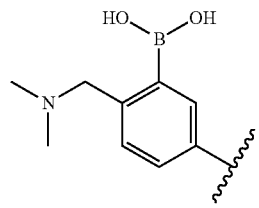(V)

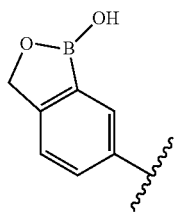(IV)

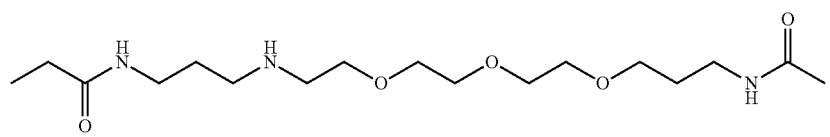(VI)

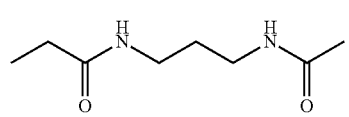(VII)

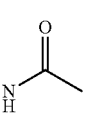(VIII)

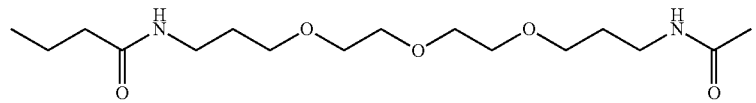(IX)

Afterwards, the BA-tosyl probe reacts with a test glycoprotein, such that a glycan residue of the test glycoprotein is covalently bound to the BA moiety via second covalent bond, the tosyl group is displaced with a nucleophilic residue of the test glycoprotein and released from the terminal azide group on the solid surface, thereby forming a first complex of the test glycoprotein and the BA-tosyl probe. In an embodiment, the first complex is immobilized on the surface via a third covalent bond.

Next, the BA-tosyl probe is released from the first complex in the presence of a releasing agent, such that the glycan residue of the test glycoprotein is exposed. In an embodiment, the releasing agent is a polyol.

And then, the glycan residue of the test glycoprotein immobilized on the surface can be detected.

According to an embodiment, the aforementioned activated ester groups can include but be not limited to an aldehyde group, a carboxyl group —O-succinimide (—O—Su) group and any combination thereof.

According to an embodiment, the aforementioned terminal amine group of the amino linker is covalently bound to the part of the activated ester groups by an amide bond formation.

According to an embodiment, the aforementioned glycol solution can include but be not limited to polyol, monosaccharide or alkoxy (poly)alkylene glycol. The polyol can be exemplified as sorbitol. The monosaccharide can be galactose, mannose or glucose. The alkoxy (poly)alkylene glycol can be selected from the group consisting of methoxy monoethylene glycol, methoxy diethylene glycol, methoxy triethylene glycol (MEG), methoxy propylene glycol, methoxy dipropylene glycol, methoxy tripropylene glycol and the combination thereof.

According to an embodiment, the aforementioned first covalent bond is a boronate ester bond formed by covalently binding the tosyl group to the terminal azide group.

According to an embodiment, the aforementioned second covalent bond is a cyclic boronate diester bond formed by covalently binding the tosyl group to diol groups of the glycan residue.

According to an embodiment, the aforementioned third covalent bond is formed by the nucleophilic residue and the terminal azide group.

According to an embodiment, after the step of reacting the BA-tosyl probe with the test glycoprotein, the present method further includes to wash unbound test glycoprotein by a washing solution. In an embodiment, the washing solution is a glycerol solution with a concentration of 5% (v/v) to 15% (v/v).

Moreover, the invention further provides a detection kit of traceless labeling glycoproteins on a surface, for performing the aforementioned method.

With application to the present method, the BA-tosyl probe can bring a test glycoprotein immobilized on a surface and expose a glycan residue of the test glycoprotein, so as to detecting the glycan residue of the test glycoprotein without altering native glycan structures.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 6(a) is a bar diagram of unblocking of the RNase B-treated BA-tosyl microarray by 10% glycerol, 100 mM galactose, or 100 mM sorbitol according to embodiments of the present invention;

FIG. 6(b) is Comparison of BA-tosyl- and aniline-tosyl-functionalized slides in the immobilization of RNase B according to embodiments of the present invention;

DETAILED DESCRIPTION

Figure 1:
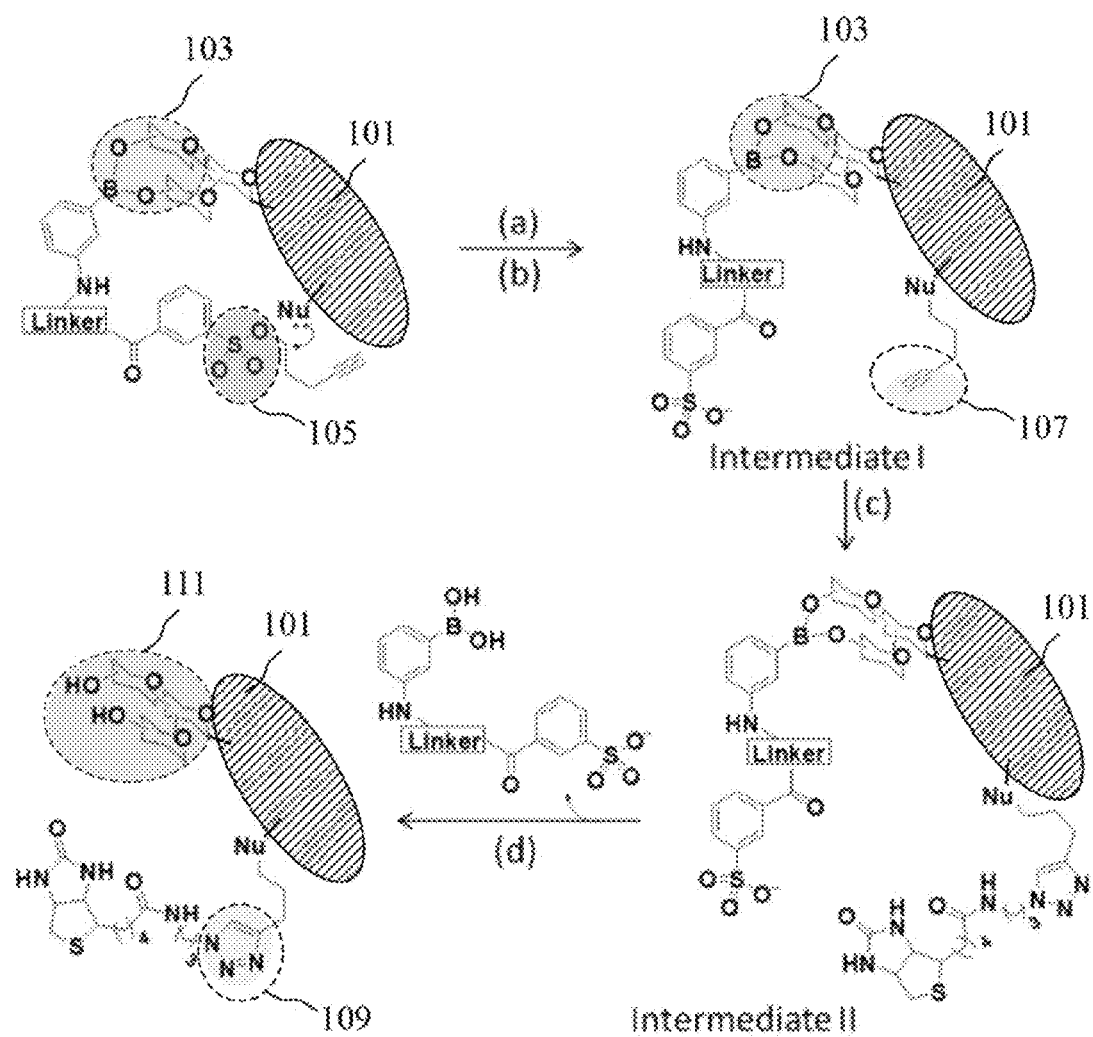
FIG. 1 is a general principle of BA-tosyl probes in the traceless labeling of glycoproteins according to one embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention relates to a method of traceless labeling glycoproteins on a surface of the present invention and the detection kit thereof, in which the BA-tosyl probe is used to bring a test glycoprotein immobilized on a surface and to expose a glycan residue of the test glycoprotein, so as to detecting the glycan residue of the test glycoprotein without altering native glycan structures.

Typically, "glycoprotein" as discussed hereinafter denotes an amino acid sequence and one or more oligosaccharide (glycan) structures associated with the amino acid sequence. The glycoproteins can exist in any sample, being purified or unpurified. The advantages of using the unpurified glycoproteins, i.e. omitting a step of glycoprotein purification, in the following glycosylation analysis can be a reduced time required for a sample preparation and a reduced amount of a sample material used. The sample can be, for example, a sample of a body tissue or a sample of a body fluid such as whole serum, blood plasma, synovial fluid, urine, seminal fluid or saliva.

The "BA-tosyl probe" as discussed hereinafter denotes the one has a structure listed as formula (II):

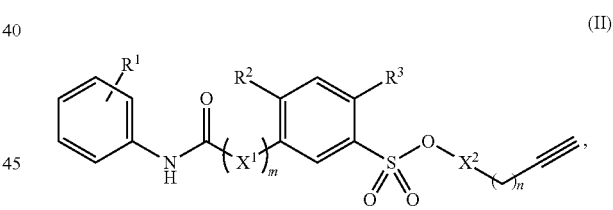

(II)

in the formula (II), the $R^1$ is a boron-containing group, and more preferably a boronic acid, a boroxole or a Wulff-type BA. In an example, an aromatic group having the $R^1$ group in the formula (II) can represent a structure listed as formulas (III) to (V). The $R^2$ is a hydrogen atom, a halide atom or an alkyl group having 1 to 3 carbon numbers. The $R^3$ is a hydrogen atom or a halide atom. The $X^1$ represents $-R^4{}_a R^5-$, the $X^2$ represents $-R^6{}_p R^7{}_q-$. The $R^4$ has a structure listed as formula (VI), the $R^5$ has a structure listed as formula (VII), the $R^6$ has a structure listed as formula (VIII), and the $R^7$ has a structure listed as formula (IX). The m represents an integer of 0 or 1, the n represents an integer of 1 to 12 and more preferably 3 to 12. The a, p or q independently and individually represents an integer of 0 or 1.

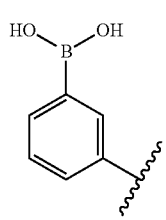 (III)
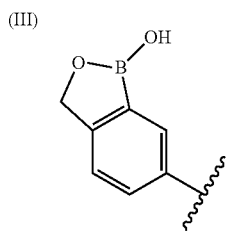 (IV)
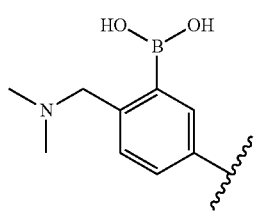 (V)
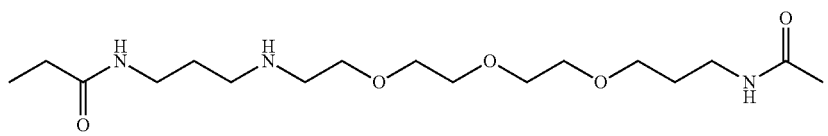 (VI)
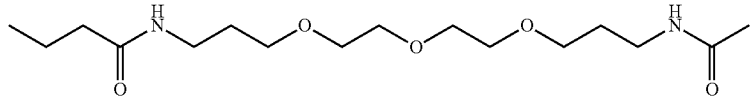 (VII)
 (VIII)
(IX)
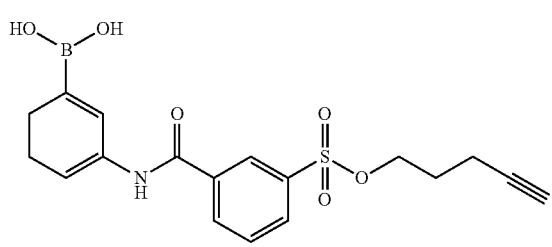
Preferably, when the R¹ is the boron-containing group as formula (III), examples of the BA-tosyl probe listed as formula (II) include but are not limited to the structures of formulas (II-1) to (II-7):
(II-1)
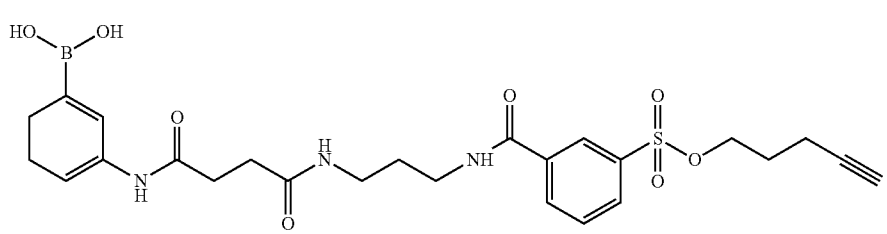
(II-2)

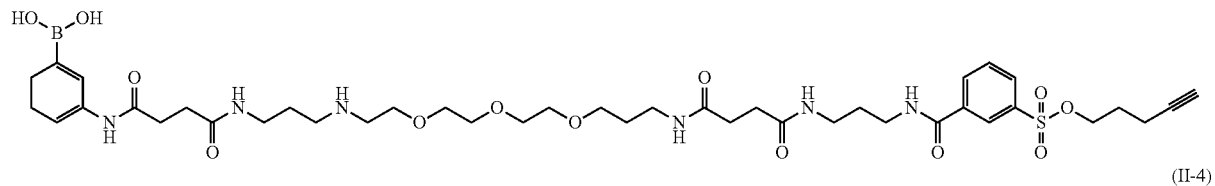
(II-3)
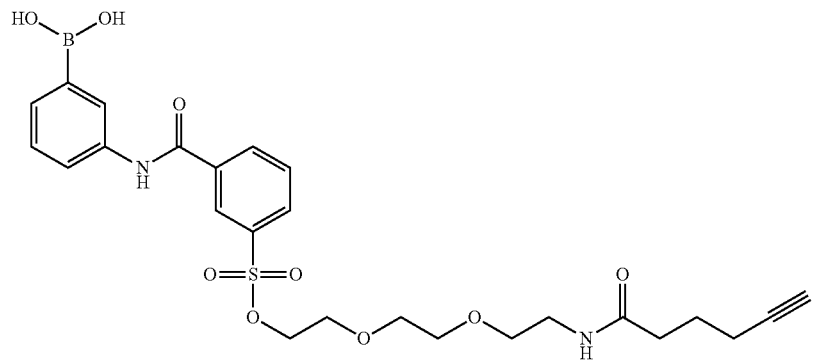
(II-4)
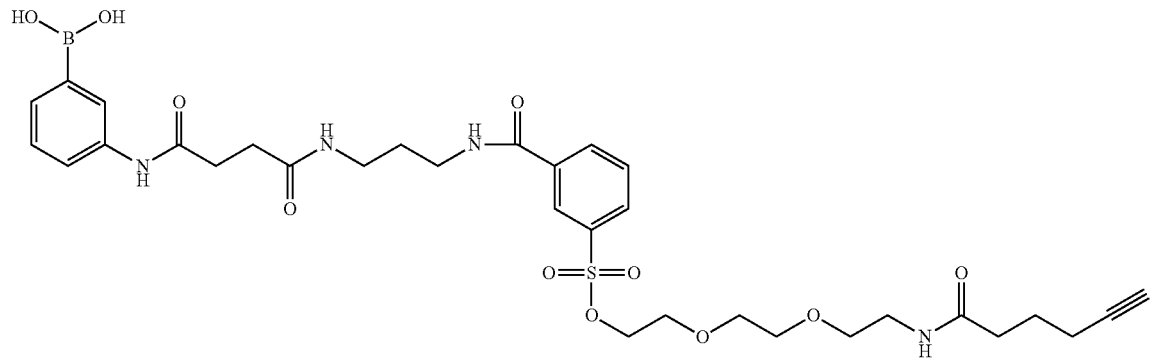
(II-5)
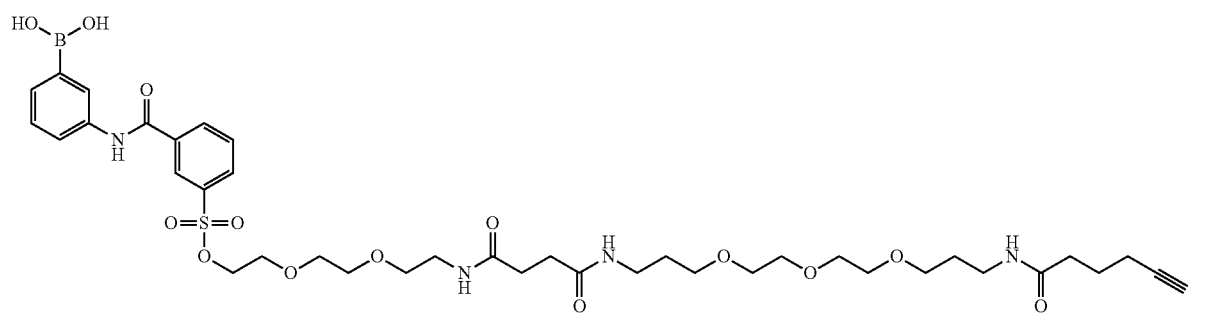
(II-6)
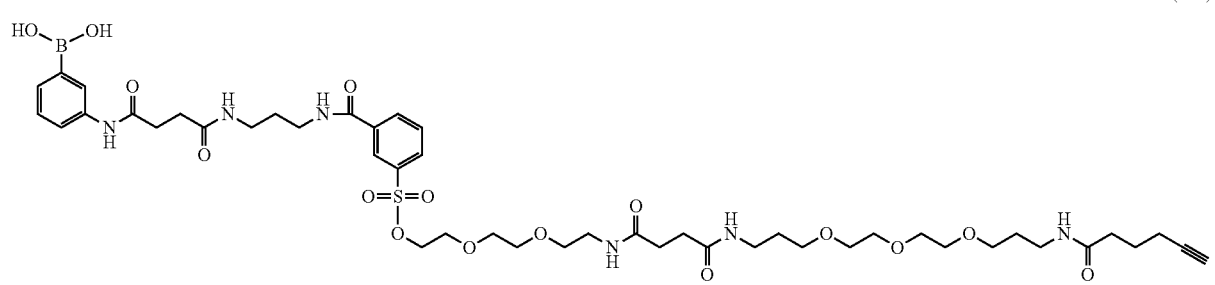
(II-7)

In the BA-tosyl probe of formula (II), boronic acid (BA) acts an affinity head to target diols of carbohydrates and form cyclic boronate diesters, in a concept similar to the "traceless labeling of glycoproteins" as discussed hereinafter.

The "immobilized" as discussed hereinafter is referred to that the BA-tosyl probe is immobilized on the surface via a first covalent bond, or a first complex of the test glycoprotein and the BA-tosyl probe is immobilized on the surface via a third covalent bond. In an embodiment, the first covalent bond is a boronate ester bond formed by covalently binding the BA-tosyl molecule to the terminal azide group, and the third covalent bond is formed by the nucleophilic residue and the terminal azide group.

In an embodiment, the BA-tosyl probe can be immobilized on the surface that has activated ester groups coated thereon. In an example, the activated ester groups can include but be not limited to an aldehyde group, a carboxyl group, —O-succinimide (—O—Su) group or any combination thereof.

The BA-tosyl probe can react with a test glycoprotein, such that a glycan residue of the test glycoprotein is covalently bound to the BA moiety via second covalent bond. In an example, the second covalent bond is a cyclic boronate diester bond formed by covalently binding the tosyl group to diol groups of the glycan residue.

The "exposed" glycan residue of the test glycoprotein as discussed hereinafter denotes that the glycan residue of the test glycoprotein immobilized on the solid surface can be detected by using conventionally tagging methods without altering native glycan structures. The ways of altering native glycan structures include any known treatments, for example, cleavage, digestion, oxidation, reduction, deoxygenation, alkylation, acylation, sulfation, phosphorylation, substituting or other treatments to modify the glycan structures of the test glycoprotein, resulting in the altered glycan structures that are different from or irreversible to the original structures of the test glycoprotein.

The present method can elevate the accuracy of detecting the exposed glycan residue of the test glycoprotein by two treatments. In the case of the solid surface with activated ester groups coated thereon, after reacting "a part of" the activated ester groups on the solid surface with the amino linker, a first blocking agent is used to block "the other part of" activated ester groups by a first blocking agent. In an example, the other part of the activated ester groups are "unreacted" with the terminal amine group of the amino linker. In some examples, the first blocking agent can be a glycol solution, examples of which can be polyol, monosaccharide or alkoxy (poly)alkylene glycol. The polyol can be exemplified as sorbitol. The monosaccharide can be galactose, mannose or glucose. The alkoxy (poly)alkylene glycol can be include but be not limited to methoxy monoethylene glycol, methoxy diethylene glycol, methoxy triethylene glycol (MEG), methoxy propylene glycol, methoxy dipropylene glycol, methoxy tripropylene glycol and any combination thereof.

In the present invention, boronic acid (BA) acts an affinity head to target diols of carbohydrates and form cyclic boronate diesters, in a concept similar to the traceless labeling of glycoproteins. Reference is made to FIG. 1, which shows a general principle of BA-tosyl probes in the method of traceless labeling of glycoproteins" according to one embodiment of this invention. In FIG. 1, the slashes-filled oval denotes the test glycoprotein 101. The dotted circle indicated as the arrow 103 denotes the cyclic boronate diester. The reactive tosylate group is marked in the gray color indicated as the arrow 105, the reporter-building core alkyne group is marked by a dotted circle 107, the triazole group is marked by a dotted circle 109, and the exposed glycan residue is marked by a dotted circle 111. The step (a) refers to a BA-directed boronate formation. The step (b) refers to a proximity effect-induced $S_N2$ reaction. The step (c) refers to Cu(I)-catalyzed cycloaddition for biotin conjugation. The step (d) refers to cleavage of boronate by treatment with polyols and the triazole group 109.

As illustrated in FIG. 1, the BA ligand triggers a specific conjugation to the glycan so the BA-tosyl molecular probe can be held in close proximity to the molecular surface of the boronated glycoproteins, as shown in the step (a) of FIG. 1. The BA targeting head is linked to a reactive tosyl group carrying a terminal alkyne; the type of linker controls the distance between the glycan and the conjugation site. The formation of the boronate diester induces a proximity effect that facilitates an $S_N2$ substitution reaction with a nucleophilic residue (Nu:) on the glycoprotein, with the release of the tosylate, as shown in the step (b) of FIG. 1. This results in the alkyne group 107 being covalently transferred onto the surface of the glycoprotein as a building core, resulting in intermediate I.

Next, the alkyne group can then react with various azido molecules via bioorthogonal Cu(I)-catalyzed 1,2,3-triazole cycloaddition. In an example, the alkyne group on intermediate I is treated with azide-functionalized biotin in the presence of $CuSO_4$ and the reducing agent tris(2-carboxyethyl)phosphine (TCEP) to give the biotinylated intermediate II, as shown in the step (c) of FIG. 1. The detail of Cu(I)-catalyzed 1,2,3-triazole cycloaddition is described later.

And then, treatment with polyols such as glycerol or sorbitol can cleave the cyclic boronate seen in intermediate II, resulting in free BA and the native glycan, as shown in the step (d) of FIG. 1. The terminal alkyne group will readily react with diverse azido molecules. In addition to the conjugation of biotin, groups such as organic fluorophores and radioactive isotopes can be added, which can be used to track, locate, and quantitatively analyze glycoproteins of interest.

In summary, the present method uses the BA-tosyl probe immobilized on the solid surface and exposes its BA moiety, so as to capture glycan residues of the test glycoprotein and to form the cyclic boronate diester bond between the BA-tosyl probe and the test glycoprotein. Upon the nucleophilic attack, the BA-tosyl probe is synchronously left from the solid surface, and the test glycoprotein is immobilized onto the solid surface. After a competitive displacement with the releasing agent, the BA-tosyl probe is released, the native glycans of the test glycoprotein is recovered and the immobilization of the test glycoprotein is finished.

Thereinafter, various applications of the method of traceless labeling glycoproteins on a surface and applications thereof will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

EXAMPLE 1

Synthesis of BA-Tosyl Probes 1, 2, and 3

Figure 2:
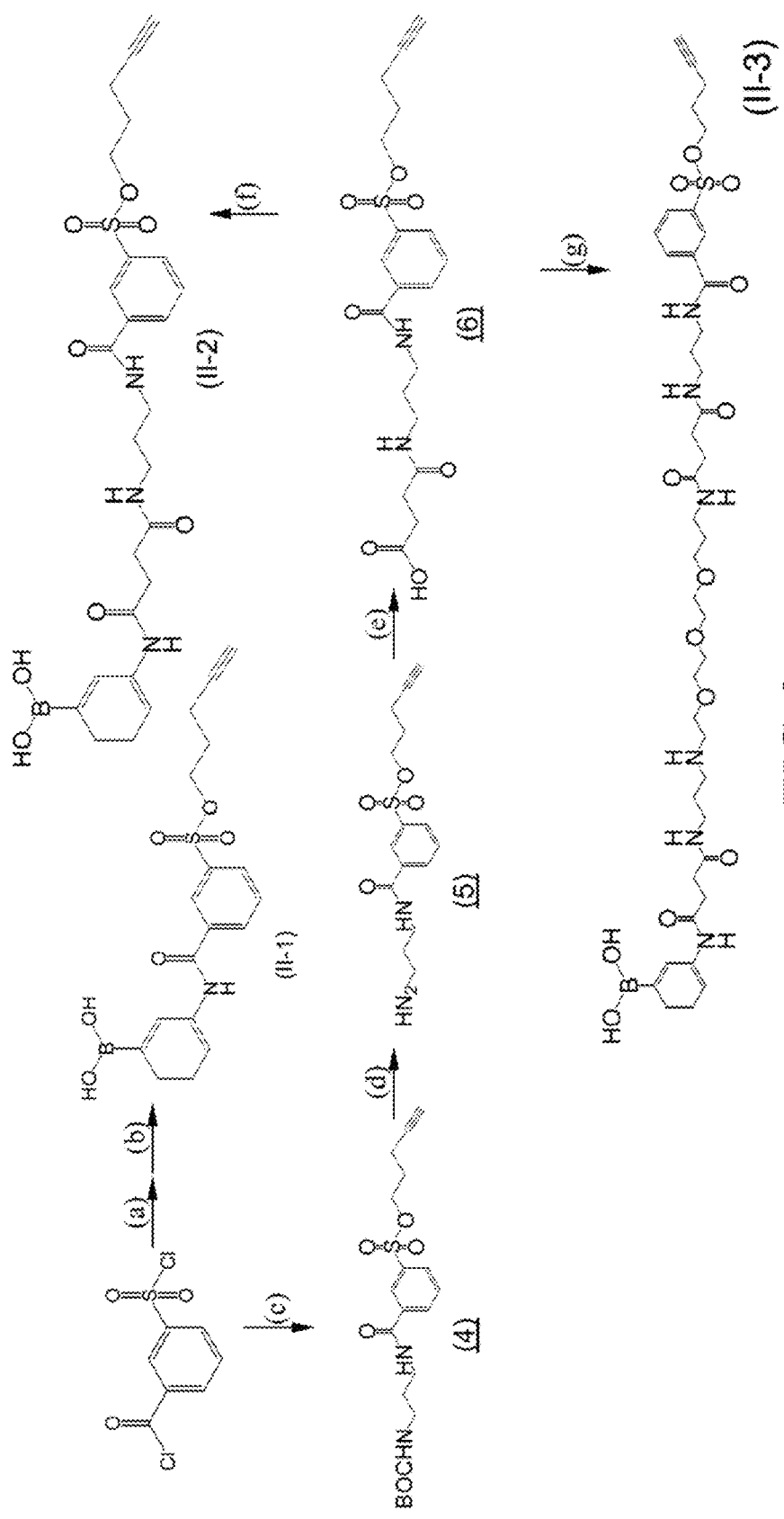
FIG. 2 is a scheme of synthesis of BA-tosyl compounds 1-3 according to embodiments of the present invention.

Reference was made to FIG. 2, which depicts a scheme of synthesis of BA-tosyl compounds 1-3 according to embodiments of the present invention. Linkers of three different lengths were incorporated into the molecular structures of three BA-tosyl probes BA-tosyl 1 (shortest), BA-tosyl 2 (medium) and BA-tosyl 3 (longest). As illustrated in FIG. 2, the use of the reactive 3-(chlorosulfonyl)benzoyl chloride (CSBC) initiated an elegant synthesis of BA-tosyl probes using a one-pot, two-step strategy. The concise synthetic approach promised the acquisition of BA-tosyl 1 by sequential treatment of the CSBC with 3-aminophenylboronic acid and 4-pentyn-1-ol in the presence of diisopropylethyl amine (DIEA) and 4-dimethylaminopyridine (DMAP). In the preparation of the BA-tosyl analogues 2 and 3 by the same method, no separable products could be obtained. After a survey of several BA protecting groups, including 1,8-diaminonaphthalene and pinacol, only very few products could be identified. Considering the difficulty in purification and the unexpected side reactions of BA-containing molecules, a new synthetic route was defined to postpone assembly of the BA groups in BA-tosyl 2 and 3 until the last step. Therefore, a Boc-protected diamine linker (tert-butyl-3-aminopropylcarbamate) was reacted with CSBC followed by the addition of 4-pentyn-1-ol. The resultant compound 4 was then deprotected by trifluoroacetic acid (TFA) to obtain compound 5 with a terminal amino group. Subjection of the amino group to succinic anhydride successfully afforded the key intermediate 6, bearing a carboxylate group. Subsequently, 3-aminophenylboronic acid was coupled to compound 6 in the presence of O-benzotriazole-1-yl-N,N,N',N'-tetramethyl-uronium-hexafluoro-phosphate (HBTU) and DIEA to produce BA-tosyl 2. Under the same conditions, an amino BA derivative (BA-TEG-amine) bearing a triethylene glycol spacer was employed to produce BA-tosyl 3.

Figure 5:
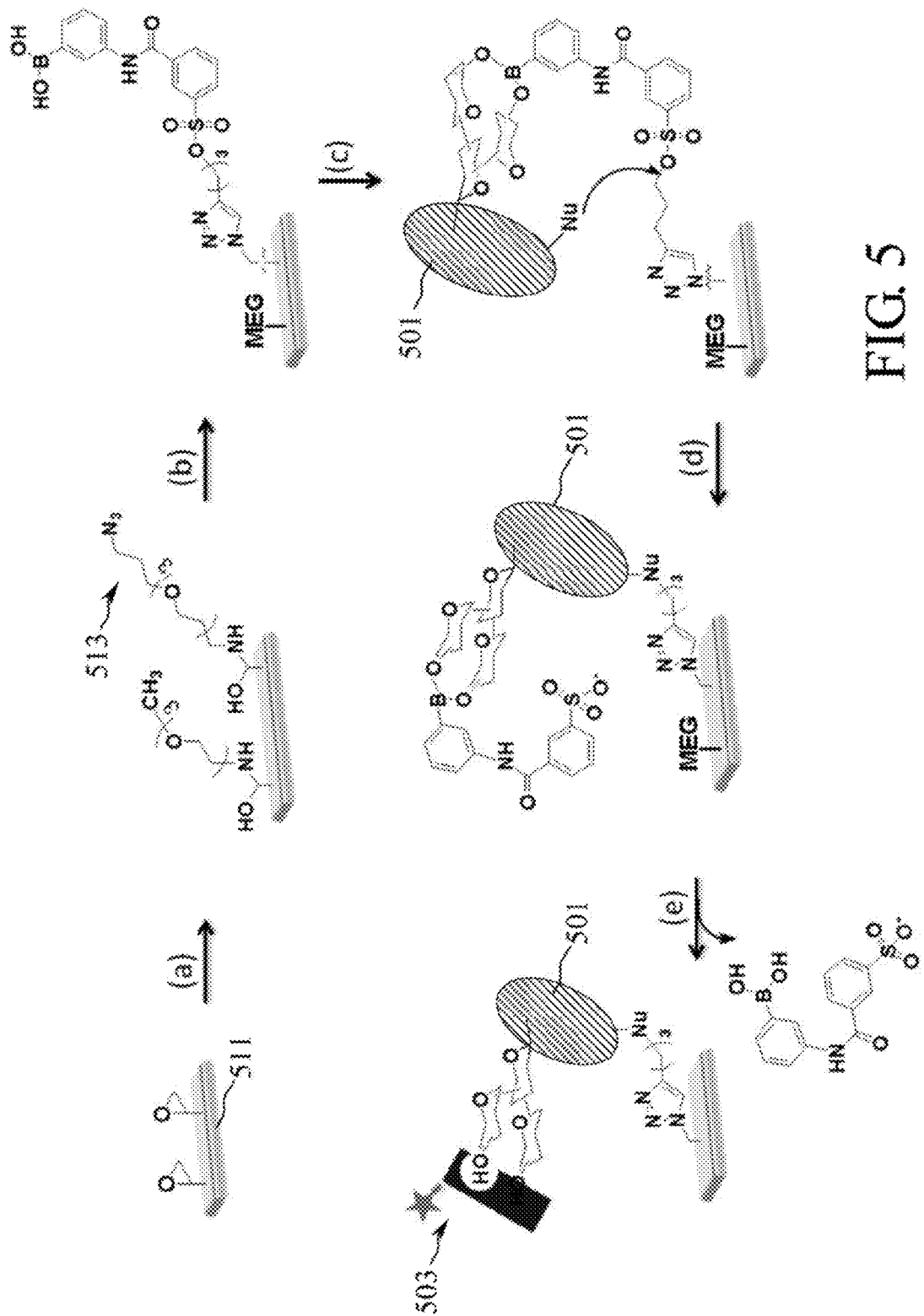
FIG. 5 is a flow chart of the fabrication of a BA-tosyl-directed glycoprotein microarray and its application in the evaluation of glycoprotein-lectin (carbohydrate-binding protein) interactions according to an embodiment of the present invention.

The details of the synthesis of BA-TEG-amine are described in FIG. 5, which was a flow chart of the fabrication of a BA-tosyl-directed glycoprotein microarray and its application in the evaluation of glycoprotein-lectin (carbohydrate-binding protein) interactions according to an embodiment of the present invention. More details are described in Yang Y.-L. et al. (2014) published in *ACS Chem. Biol.* 9(2):390-397, titled as "Traceless Labeling of Glycoproteins and Its Application to the Study of Glycoprotein-Protein Interactions", which is incorporated as reference in the present invention In FIG. 5, the slashes-filled oval denoted the test glycoprotein 501. A solid block with a star denoted the fluorescently labeled lectin 503, and MEG denotes methoxy triethylene glycol. An epoxy slide denoted a commercially available epoxy slide 511. The arrow indicated an amino linker 513.

The poor yields of the last coupling reactions were attributed to the need for a low reaction concentration to prevent the undesired $S_N2$ reaction by the amine with the tosyl group and the considerable loss of product during column chromatography.

EXAMPLE 2

Evaluation of the Specificity of BA-Tosyl Probes in the Traceless Labeling of Glycoproteins To evaluate the applicability of BA-tosyl 1-3 in the specific labeling of glycoproteins, two negative control compounds, aniline-tosyl 7 and BA-alkyne 8, were synthesized and used to validate the necessity of both the BA group and the tosyl group in this traceless labeling strategy. Chemical structures of two control molecules, aniline-tosyl 7 and BA-alkyne 8 were listed as the following formula (X) and formula (XI), respectively:

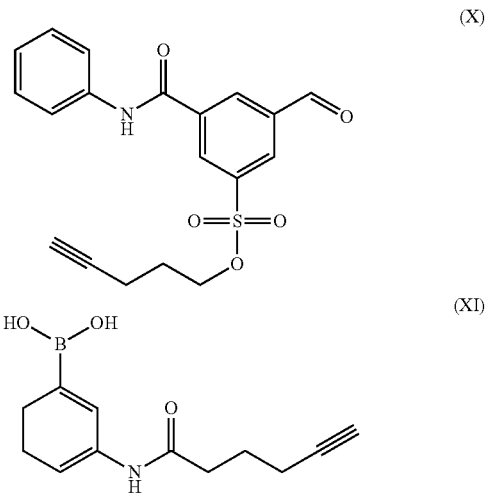

Preparation of Fetuin-Spiked BL21 Crude Cell Lysate

BL21 *E. coli* cells were inoculated in lysogeny broth (LB) medium at 37° C. until the $OD_{600}$ reached 0.8. Then, the cells were collected by centrifugation at 6,000 rpm below 4° C. for 15 min, and cell pellets were obtained by decanting the supernatant. After lysing by ultrasonication, the supernatant, composed of numerous proteins, was collected after centrifugation at 15,000 rpm for 30 min. The obtained cell lysates were spiked with fetuins (stock solution, 1 mM) to give fetuin concentrations of 10 μM, 1 μM, and 0.1 μM in cell lysates.

Labeling of Fetuin by BA-Tosyl Probes

A solution of fetuins (10 μM) was incubated with BA-tosyl probes 1-3 (50 μM) in PBS buffer (0.1 M, pH 8.0) at 37° C. for 48 h. Then, the unreacted BA-tosyl probes were removed by centrifugal filtration (Amicon Ultra-0.5 mL 10K) at 15,000 rpm, followed by washing five times with PBS buffer (300 μL). The resultant alkyne-tagged fetuins (11.53 μL, 26.28 μg/μL) were collected and treated with azido biotin (20 μL, 1 mM) in PBS buffer (44.47 μL, pH 8.0, 0.1 M). Then, the mixture was treated with tris(carboxyethyl)phosphine (TCEP, 0.1 M, 2 μL) and tris[(1-benzyl-1H-1,2,3-triazol-4-yl)methyl]amine (TBTA, 0.01 M, 20 μL) with gentle shaking. After homogeneous mixing, $CuSO_4$ (0.1 M, 2 μL) was added, and the reaction mixture was shaken at RT for 12 h. The excess reactants were removed by centrifugal filtration at 15,000 rpm, and the biotinylated fetuins were obtained.

General Methods and Materials $^1$H and $^{13}$C NMR spectra were acquired at 300 and 75 MHz, respectively (unless otherwise indicated), relative to $CDCl_3$ (7.26 ppm, $^1$H NMR; 77.0 ppm, $^{13}$C NMR) and $d_4$-methanol (3.31 ppm, $^1$H NMR; 49.15 ppm, $^{13}$C NMR). Flash chromatography was performed using silica gel (43-60 μM, Merck). Monomeric acrylamide/bisacrylamide solution (40%, 29:1) was purchased from Bio-Rad. BCA and Bradford protein assay kits were obtained from Pierce. Sodium dodecyl sulfate (SDS) was purchased from GE Healthcare. All other chemicals and solvents were purchased from Sigma-Aldrich and Acros. Fetuin (from fetal calf serum) and RNase B (from bovine pancreas) were purchased from Sigma-Aldrich. The epoxy slides were purchased from Arrayit (Sunnyvale, Calif., USA). Goat anti-bovine lactoferrin antibody was purchased from Bethyl Laboratories (Montgomery, Tex., USA), and monoclonal anti-biotin antibody (peroxidase conjugated) for Western blotting was purchased from Sigma-Aldrich. Water was obtained from a Milli-Q Ultrapure water purification system (Millipore, Billerica, Mass.).

To evaluate the specificity of synthetic BA-tosyl probes, BA-tosyl 1-3, aniline-tosyl 7, and BA-alkyne 8 (40 μM) were incubated with fetuins (20 μM), blood glycoproteins carrying triantennary glycan chains with terminal N-acetylneuraminic acids, at 37° C. for 48 h. The unreacted chemical probes were then removed by centrifugal filtration or size-exclusion column chromatography to obtain the alkyne-labeled fetuins. Azido biotin was then used to form biotinylated fetuins via Cu(I)-catalyzed 1,2,3-triazole cycloaddition. Polyacrylamide gel electrophoresis (SDS-PAGE) followed by Western blotting with an antibiotin monoclonal antibody (peroxidase-conjugated) provided direct evidence of the irreversible and covalent biotin labeling of the fetuins, as shown in FIG. 3.

Figure 3:
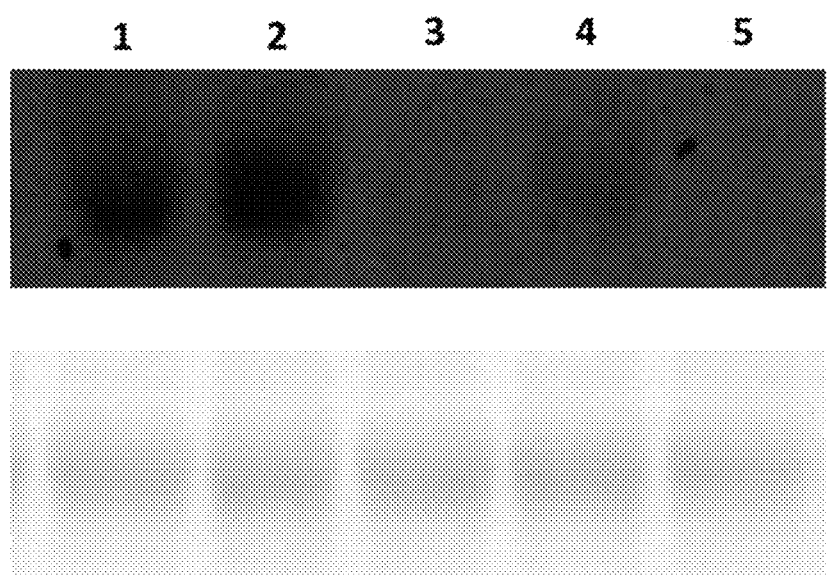
FIG. 3 is images of SDS-polyacrylamide gel electrophoresis (SDS-PAGE, below) and western blotting (above) of fetuins after treatment with each BA-tosyl and with control compounds followed by biotinylation according to an embodiment of the present invention.

In FIG. 3, Coomassie blue staining of the SDS-PAGE gel (below) shows that there were equal amounts of fetuin in each lane. The signal in the upper part of the figure was revealed by Western blotting with an anti-biotin monoclonal antibody. Lanes 1 to 5 represent the results of fetuins treated with BA-tosyl 1 (formula (II-1)), BA-tosyl 2 (formula (II-2)), BA-tosyl 3 (formula (II-3)), aniline-tosyl 7 (formula (X)) and BA-alkyne 8 (formula (XI)) probes, respectively.

In FIG. 3, a very weak band in lane 4 and no distinguishable band in lane 5 clearly indicated that both the BA and tosyl groups were essential for the specific labeling of glycoproteins, whereas the strong band in lane 2 showed the successful labeling of fetuins by BA-tosyl 2. The labeling efficiency of fetuin was determined by separating the biotinylated fetuin and unlabeled fetuin using streptavidin-coated beads (Pierce high capacity streptavidin agarose bead) and then quantitatively analyzing the protein by a BCA assay. This gave a labeling efficiency of 67%. An increase in molecular weight of fetuin after labeling has been observed by MALDIMS, shown in Figure S3 of Supporting Information (at http://pubs.acs.org/doi/suppl/10.1021/cb400631w/suppl_file/cb400631w_si_001.pdf), which was incorporated as reference in the present invention. Compared to BA-tosyl probes, aniline-tosyl 7 produced a much weaker signal, which demonstrated the crucial role of the BA group in the recognition of glycoproteins.

To further validate the role of the tosyl group, BA-alkyne 8 was treated with fetuins under the same conditions. In principle, the function of the BA group was for the specific recognition of glycans and the mediation of the formation of boronate diester bonds; however, in the presence of glycerol during SDS-PAGE and Western blotting analysis, the reversibility of the boronate diester formation allowed facile recovery of the native glycans and BA. As a result, no distinguishable band was seen in lane 5 of FIG. 3, which definitely confirmed the requirement for a reactive tosyl group to furnish stable and irreversible covalent conjugation. Compared to the BA-tosyl 2 labeling of fetuin (lane 2 of FIG. 3,), much less labeling was observed with BA-tosyl 1. An appropriate spacer between the BA headgroup and the reactive tosyl group could modulate the spatial distance between the glycan and the reporter. A longer spacer may cover a larger area to reasonably increase the labeling efficiency. However, BA-tosyl 3, with the longest linker, afforded very poor labeling of fetuins (lane 3 of FIG. 3). The longer linker has a higher degree of freedom and thereby reduces the efficiency of proximity-promoted conjugation. Therefore, the need for higher energy after the formation of boronate diester bonds may considerably affect the key $S_N2$ reaction step in the case of BA-tosyl 3.

Figure 4A:
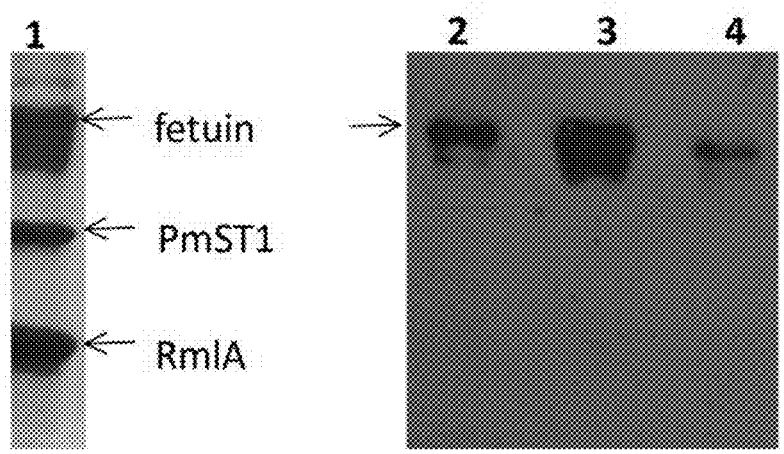
FIG. 4(a) is a SDS-PAGE analysis of a mixed protein pool with Coomassie blue staining (lane 1) and after Western blotting (lanes 2-4), after the mixed pool was treated with BA-tosyl 1 (lane 2), BA-tosyl 2 (lane 3), and BA-tosyl 3 (lane 4) according to embodiments of the present invention.

After successful labeling of fetuins, a mixed protein pool containing two nonglycosylated recombinant proteins, α-2, 3-sialyltransferase (PmST1, 43 kDa) and glucose-1-phosphate thymidyltransferase (RmlA, 33 kDa), and the glycosylated fetuin, all at the same concentration of 10 μM, was prepared and incubated with BA-tosyl 1-3 to evaluate their specificities in a mixed pool of proteins containing large amounts of undesired proteins (FIG. 4(a), lane 1). After removing unreacted probes and after biotin conjugation processing, a single band was seen by Western blotting, indicating the high selectivity of the BA-tosyl probes for fetuins, even in the presence of two other nonglycosylated proteins. In agreement with the previous results, BA-tosyl 2 gave the strongest band (FIG. 4(a), lane 3), which clearly demonstrated its efficiency and specificity in the recognition of fetuins compared to BA-tosyl 1 and 3. Treatment with BA-tosyl 1 resulted in a weak band in lane 2, corroborating the result in FIG. 3, lane 1. The much weaker band shown in lane 4 indicated the poor efficiency of BA-tosyl 3-directed fetuin labeling in a mixed system, consistent with it is weak labeling of pure fetuins in FIG. 3, lane 3.

Figure 4B:
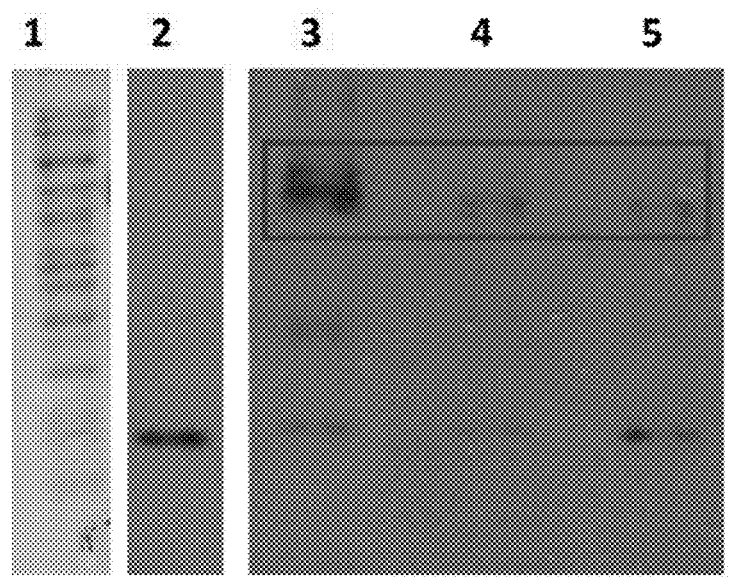
FIG. 4(b) is a SDS-PAGE analysis of a BL21 crude cell lysate with Coomassie blue staining (lane 1) and Western blotting by monoclonal antibiotin antibody (lanes 2-5) according to embodiments of the present invention.

To further demonstrate the specificity of BA-tosyl probes, fetuins were mixed with a real biofluid containing highly abundant undesired proteins. A crude *E. coli* lysate (strain BL21, known to be entirely deficient in post-translational glycosylation) containing a total of 118 μg of various proteins was mixed with fetuins to produce final fetuin concentrations of 10, 1, and 0.1 μM. BA-tosyl 1 and 2 were then individually incubated with the fetuin-spiked cell lysates at 37° C. for 48 h. After removal of unreacted probe, the mixtures were analyzed by SDS-PAGE and Western blotting, as shown in FIG. 4 (b). In FIG. 4 (b), crude cell lysate was spiked with varying amounts of fetuins and treated with BA-tosyl 2 (lane 3: $10^{-5}$ M fetuins; lane 4: $10^{-6}$ M fetuins; lane 5: $10^{-7}$ M fetuins). Lane 2 was a control lane of crude cell lysate with no added fetuins.

Compared to the negative control of native cell lysates without added fetuins (lane 2), BA-tosyl 2 (lanes 3-5) in FIG. 4 (b), it still delivered specific labeling of the desired fetuins with only a slight background observed; however, BA-tosyl 1 showed no observable signal (see Figure S1 of Supporting Information at http://pubs.acs.org/doi/suppl/10.1021/cb400631w/suppl_file/cb400631w_si_001.pdf).

The results, showing specific labeling of glycoproteins in both a mixed pool of proteins and in a crude cell lysate, definitely support the use of BA-tosyl probes as powerful tools in the discovery of glycoproteins and inspired us to apply the probes to the evaluation of glycoprotein-protein interactions. Although BA-tosyl 2 satisfied the need for specificity in the labeling of fetuins, BA-tosyl 1 and 3 may be ideal probes in labeling other glycoproteins. In practical use, a mixed probe pool including BA-tosyl 1, 2, and 3 might be an ideal tool to enrich glycoproteins from unknown samples.

EXAMPLE 3

Preparation of BA-Tosyl Functionalized Slides
Preparation of Azide-Functionalized Slides The epoxy slides (Arrayit, USA, SuperEpoxy substrate slide (protein)) were rinsed twice with DMF (10 mL) and immersed in DMF (45 mL) under dry nitrogen. 3-Azidopropylamine (5 mL, 0.1 M in DMF) was added to the reaction vessel to afford a final concentration of 10 mM. The reaction was allowed to proceed at RT. After 12 h, a surface spacer, methoxy triethylene glycol (MEG, 100 mM), was added to the reaction mixture to block the unreacted epoxy groups. The resulting azide-functionalized slides were then washed three times with DMF (50 mL) and dried under a stream of nitrogen.

Cu(I)-Catalyzed 1,2,3-Triazole Cycloaddition

The aforementioned azide-functionalized slide was rinsed twice with sodium phosphate buffer (25 mM, pH 8.0) and immersed in the same buffer (45 mL). To effect the Cu(I)-catalyzed 1,2,3-triazole cycloaddition, BA-tosyl 1 (or compound 7 or 8) was added to the reaction mixture to afford a final concentration of 5 mM and treated with TCEP (2 mM) and TBTA (2 mM). Then, an aqueous solution of CuSO 4 (100 mM) was added to the reaction mixture to give a final concentration of 4 mM, and the mixture was allowed to react at RT. After 12 h, the slide was washed three times with PBS and twice with distilled deionized water ($ddH_2O$) to obtain BA-tosyl 1 (or compound 7 or 8)-functionalized slides.

Glycoprotein-Lectin Interaction with the Microarray

Fluorescein-labeled lectins (Con A-FITC and WGA-FITC, 10 μM in PBS containing 5 mM $CaCl_2$ and 5 mM $MnCl_2$) were incubated with the glycoprotein microarray at RT for 1 h. Then, the slide was washed three times with PBS containing 10% glycerol and twice with $ddH_2O$. Finally, the slide was dried under warm air and subjected to fluorescence analysis.

Protein Microarray Analysis

To quantitatively evaluate the protein-glycoprotein interactions, the lectin-glycoprotein complexes were analyzed by measuring the fluorescence intensities of the fluorescein tags. The fluorescence signals were directly detected by a NovaRay Microarray Scanner with an FITC filter, and were subsequently analyzed using ArrayVision software.

To achieving a chip-based evaluation of glycoprotein-protein interactions, a BA-tosyl-functionalized glass slide was prepared via Cu(I)-catalyzed 1,2,3-triazole cycloaddition and was subsequently used in the fabrication of glycoprotein microarrays with native glycans. The high-throughput format of protein microarrays makes them important glycobiological platforms for systematic screening of glycan-mediated inter-actions. Accordingly, a glycoprotein microarray can rapidly generate a high output of information related to the expression and structural alteration of glycans, which is very useful in clinical diagnoses.

The present invention advantageously proposes the chemoselective immobilization of glycoproteins with completely conserved glycans. Using the same concept of the BA-tosyl-directed labeling of glycoproteins, a glycosylated protein of interest can form a cyclic boronate diester, which immediately triggers an $S_N2$ reaction that covalently anchors the glycoprotein onto the glass slide. Reference was made to FIG. 5 again. For example, a commercially available epoxy slide 511 was treated with an amino linker 513 with a terminal azide functional group (FIG. 5, step (a)), and the unreacted epoxy groups were then blocked by a blocking spacer, methoxy triethylene glycol (MEG, FIG. 5, step (a)). Following treatment with BA-tosyl 1 in the presence of $CuSO_4$ and a reducing agent, the slide surface was successfully modified with BA-tosyl probes (step (b)). The exposed BA group was then responsive in the recognition of glycan residues of the test glycoprotein 501 and formed boronate diesters (step (c)). Subsequently, the nucleophilic residue (denoted as Nu) of the test glycoprotein 501 directed the second covalent conjugation and immobilized the glycoprotein 501 of interest onto the microarray (step (d)). The boronate group was then released by a simple competitive displacement with polyols to recover the native glycan residue and free the BA-tosylate byproduct. The resultant immobilized glycoprotein 501 exposes its biologically significant glycan residue for advanced studies of glycoprotein-protein interactions, for examples, being labeled by the fluorescently labeled lectin 503 (step (e)).

EXAMPLE 4

Monitoring of Glycoprotein-Protein Interactions by a Glycoprotein Microarray

BA-Tosyl-Functionalized Slide-Direction Immobilization of Glycoproteins

Glycoproteins in $ddH_2O$ containing 20% dimethyl sulfoxide (DMSO) were spotted onto the surface of the functionalized slide. To immobilize glycoproteins on the slides, an AD1500 arrayer (Biodot) was used to print samples of interest onto the functionalized slide with a spot volume of 20 nL under 85% relative humidity at 25° C. The protein sample was allowed to incubate at 25° C. for 12 h, and the glycoprotein solution was then removed by decanting the reaction mixture. The slide was incubated with $ddH_2O$ containing 10% glycerol for 30 min, followed by washing twice with the same solution ($ddH_2O$ with 10% glycerol). The slide was further treated with 10 mM imidazole solution (Tris buffer, 10 mM NaCl, pH 7.4) for 30 min to block unreacted BA-tosyl groups. The obtained glycoprotein micro-array was then washed three times by PBS (pH 7.4) and was ready for advanced use.

Glycoproteins in $ddH_2O$ containing 20% dimethyl sulfoxide (DMSO) were spotted onto the surface of the functionalized slide. To immobilize glycoproteins on the slides, an AD1500 arrayer (Biodot) was used to print samples of interest onto the functionalized slide with a spot volume of 20 nL under 85% relative humidity at RT. The protein sample was allowed to incubate at RT for 12 h; the glycoprotein solution was then removed by decanting the reaction mixture. The slide was incubated with $ddH_2O$ containing 10% glycerol for 30 min, followed by washing twice with the same solution ($ddH_2O$ with 10% glycerol). The slide was further treated with 10 mM imidazole solution (Tris buffer, 10 mM NaCl, pH 7.4) for 30 min to block unreacted BA-tosyl groups. The obtained glycoprotein micro-array was then washed three times by PBS (pH 7.4) and was ready for advanced use.

To evaluate the details of the immobilization mechanism, ribonuclease B (RNase B), carrying a single N-glycan chain composed of high mannose isomers, was spotted onto BA-tosyl-functionalized slides and allowed to incubate at 25° C. for 12 h. The slides were then individually treated with three different polyols in phosphate buffered saline (PBS) to competitively release the BA-tosylate. Glycerol (10%), galactose (100 mM), and sorbitol (100 mM) were used. Then, a specific mannose binding protein, concanavalin A (Con A), labeled with fluorescein isothiocyanate (FITC), was used to monitor binding to the unblocked mannose of immobilized RNase B, providing information regarding the RNase B and Con A-FITC interactions. Slides treated with glycerol and sorbitol performed nearly equally well, with twice the intensity from Con A-FITC compared to slides treated with galactose (FIG. 6(a)). The result demonstrated the importance of this traceless labeling strategy in maintaining the native glycan structure of immobilized RNase B, which can therefore be specifically recognized by Con A-FITC.

Figure 6:
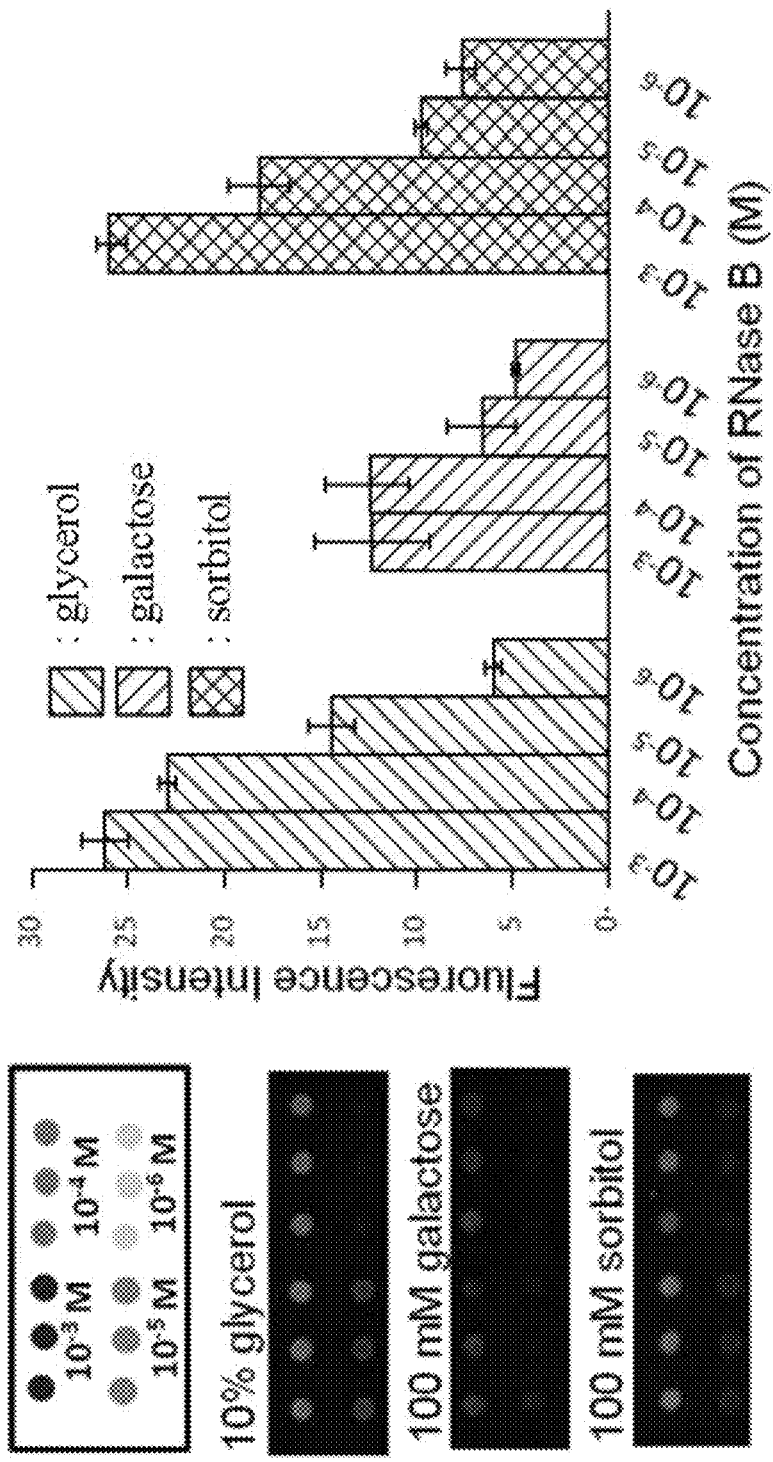
FIG. 6 (c) is Comparison of BA-tosyl- and BA-alkyne-functionalized slides in the immobilization of RNase B according to embodiments of the present invention.
Figure 6:
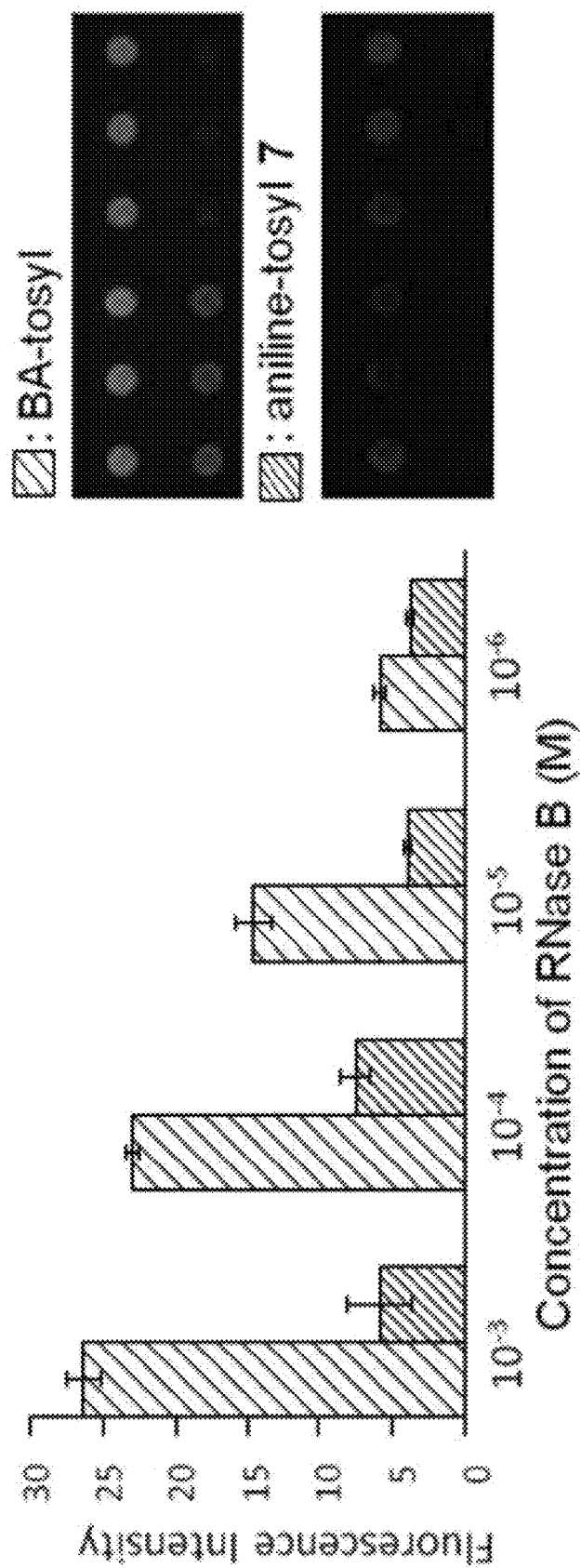
Figure 6:
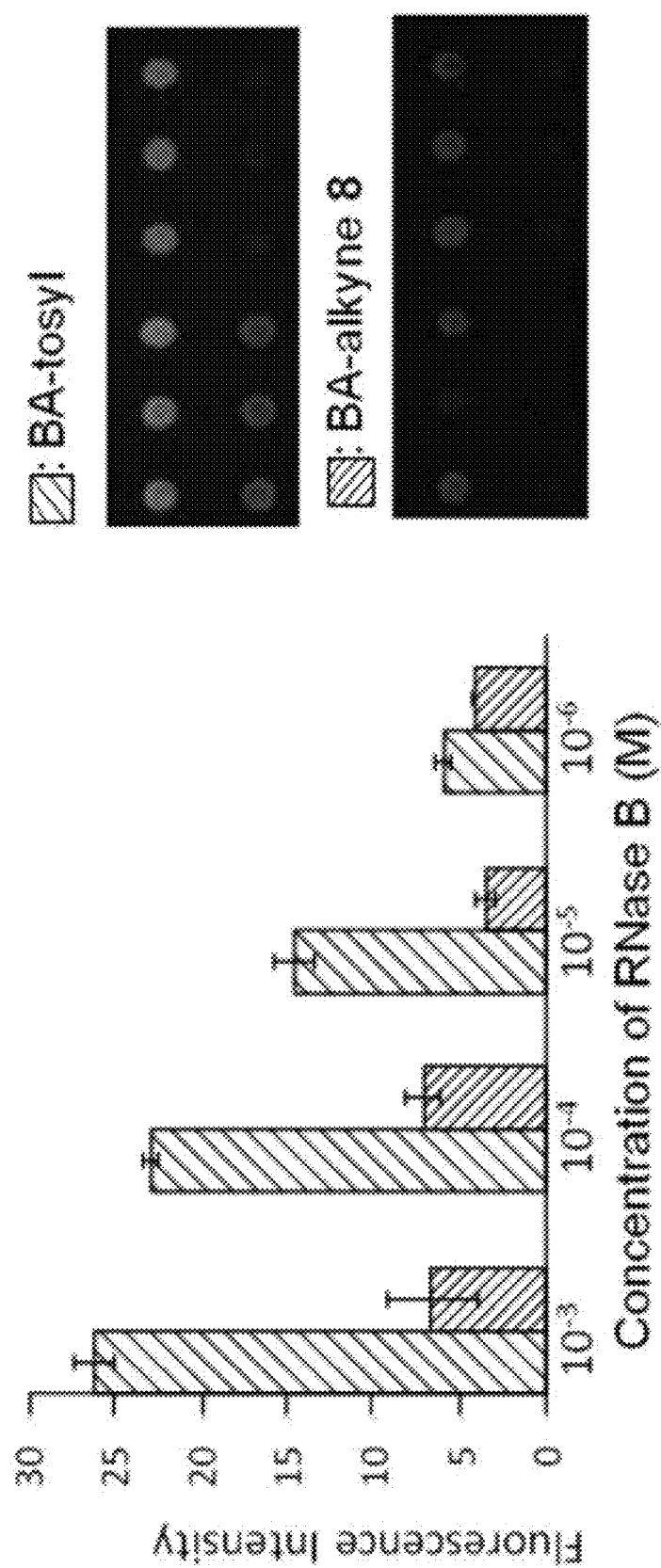

Because glycerol is generally used in protein microarray operations as a working buffer to suppress nonspecific binding without altering native protein activity, 10% glycerol in PBS is an ideal buffer to reduce background interference and simultaneously unblock the native glycans. Slides functionalized with control compounds 7 and 8 were prepared and incubated with RNase B followed by treatment with glycerol. Compared to the BA-tosyl-treated slides, aniline-tosyl 7-functionalized slides lacking the BA group showed very low signal intensity with no linear correlation in sequentially diluted RNase B, which implied that the weakly observed signals derived from nonspecific adsorption (FIG. 6(b)). In the absence of the reactive tosyl group, RNase B captured by BA-alkyne 8 leaked readily from the surface of the slides after treatment with glycerol (FIG. 6(b)). The nearly background-level signals of the control slides (compounds 7 and 8) demonstrated that both the BA and tosylate groups were essential for the newly developed fabrication of a glycoprotein microarray that can selectively direct the immobilization of native glycoproteins. The limit of detection with the glycoprotein microarray is in the range of $10^{-5}$ M glycoprotein, as shown in FIGS. 6(a) to 6(c). As the loading concentration of glycoprotein was reduced to $10^{-6}$ M, the obtained signals were very little above background.

To evaluate the applicability of the glycoprotein microarray for the analysis of glycans, two glycoproteins, RNase B and fetuin, were immobilized and their native glycans exposed for glycoprotein-protein interactions. A survey of glycan compositions showed that for RNase B they are composed of 5-9 mannose residues, while fetuins embed mannose residues in their cores and expose several N-acetylneuraminic acids at the ends of sugar chains. Fetuin, one of the major glycoproteins found in fetal calf serum, is known to contain three mucin-type sugar chains and three asparagine-linked sugar chains. Both types of sugar chains are mainly composed of N-acetylneur-aminic acid, galactose, N-acetyglucosamine, and N-acetygalac-tosamine residues. Asparagine-linked sugar chains are known to have typical triantennary and biantennary structures containing different numbers of N-acetylneuraminic acid residues.

Figures 7A, 7B:
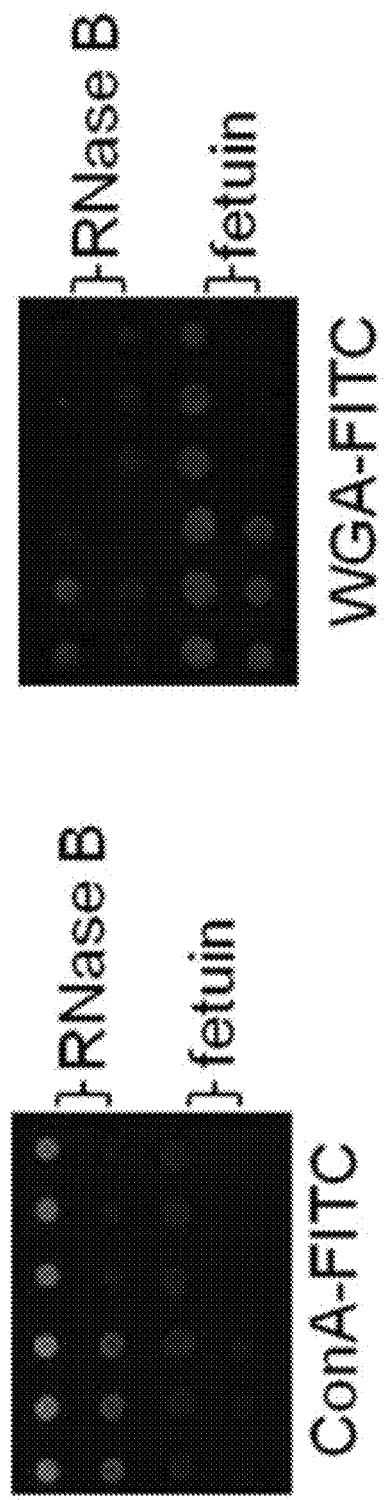
FIGS. 7(a) and 7(b) are fluorescent images of glycoprotein-lectin interactions on the glycoprotein microarrays according to embodiments of the present invention.
Figure 7:
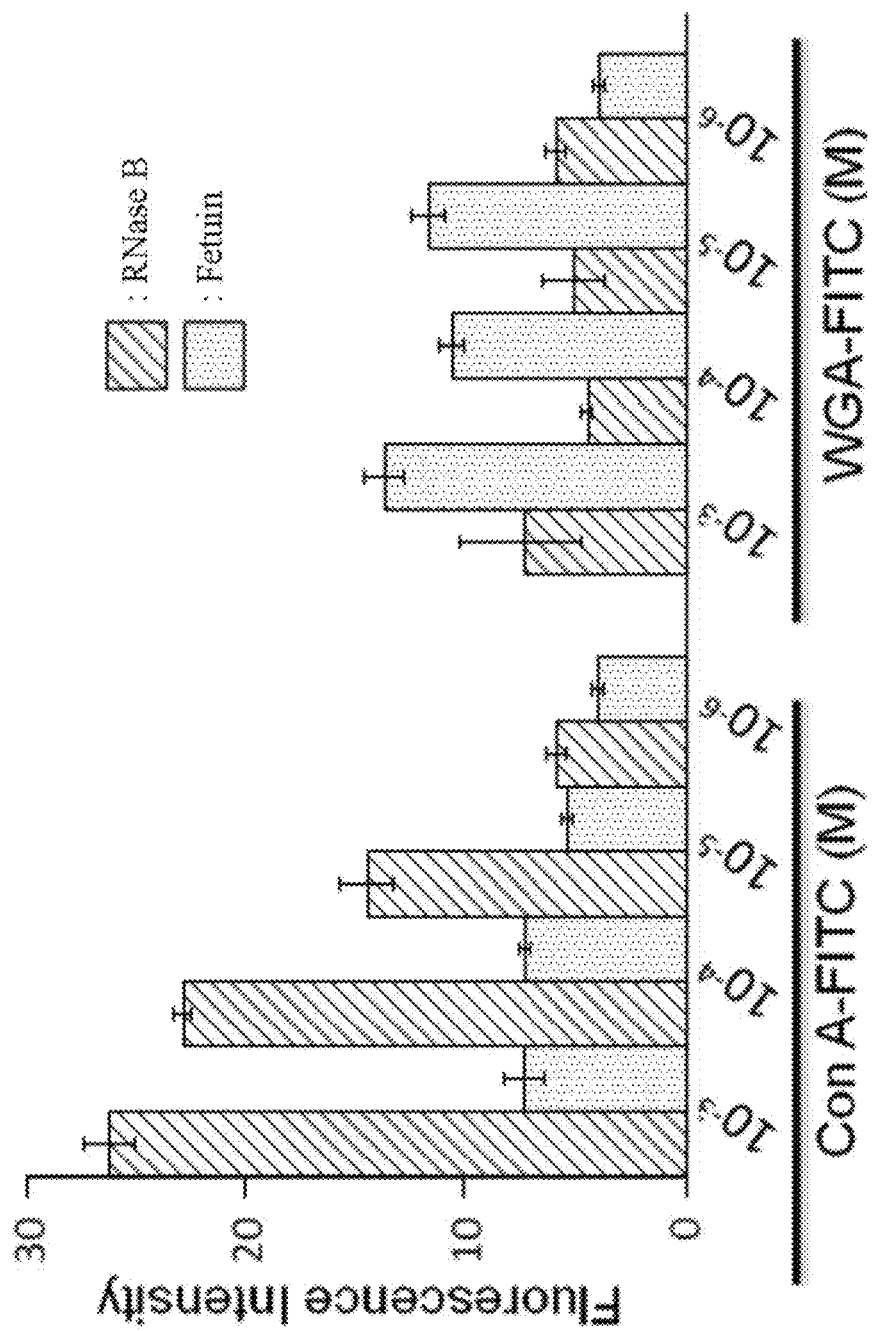
FIG. 7(c) is a bar diagram in comparison of interactions between fluorescent lectins (Con A-FITC and WGA-FITC) with glycoproteins (RNase B and fetuin) according to embodiments of the present invention.

Analysis with fluorescently labeled lectins, in FIGS. 7(a) to 7(c), showed that the embedded nature of the mannose residues of the immobilized fetuins reduced the binding affinity of Con A-FITC. Conversely, wheat germ agglutinin (WGA), an N-acetylneuraminic acid/N-acetylglucosamine binding protein, bound specifically to the terminal N-acetylneuraminic acids of fetuins and, therefore, had a signal intensity at most two times higher that of RNase B.

To further demonstrate the superiority of this method over others, a fetuin solution ($10^{-3}$ M) containing 1% BSA was simultaneously spotted onto the BA-tosyl-functionalized slide and onto the conventionally used epoxy slide. The BA-tosyl-functionalized slide successfully directed the immobilization of fetuin and gave nearly a two times higher signal intensity than the epoxy slide, shown in Figure S2 of Supporting Information at http://pubs.acs.org/doi/suppl/10.1021/cb400631 w/suppl_file/cb400631w_si_001.pdf). The better response of the BA-tosyl-functionalized slide was due to the chemoselectivity in the recognition of glycosylated fetuin but ignored the non-glycosylated BSA. On the contrary, the conventional epoxy slide had no discrimination between fetuin and BSA and therefore reduced the loading efficiency of fetuins. This result strongly supports the importance of this chemoselective strategy in the fabrication of a glycoprotein microarray from mixed samples. The BA-tosyl-directed glycoprotein microarray was elegantly used in the screening of glycan structures of glycoproteins.

Figure 8:
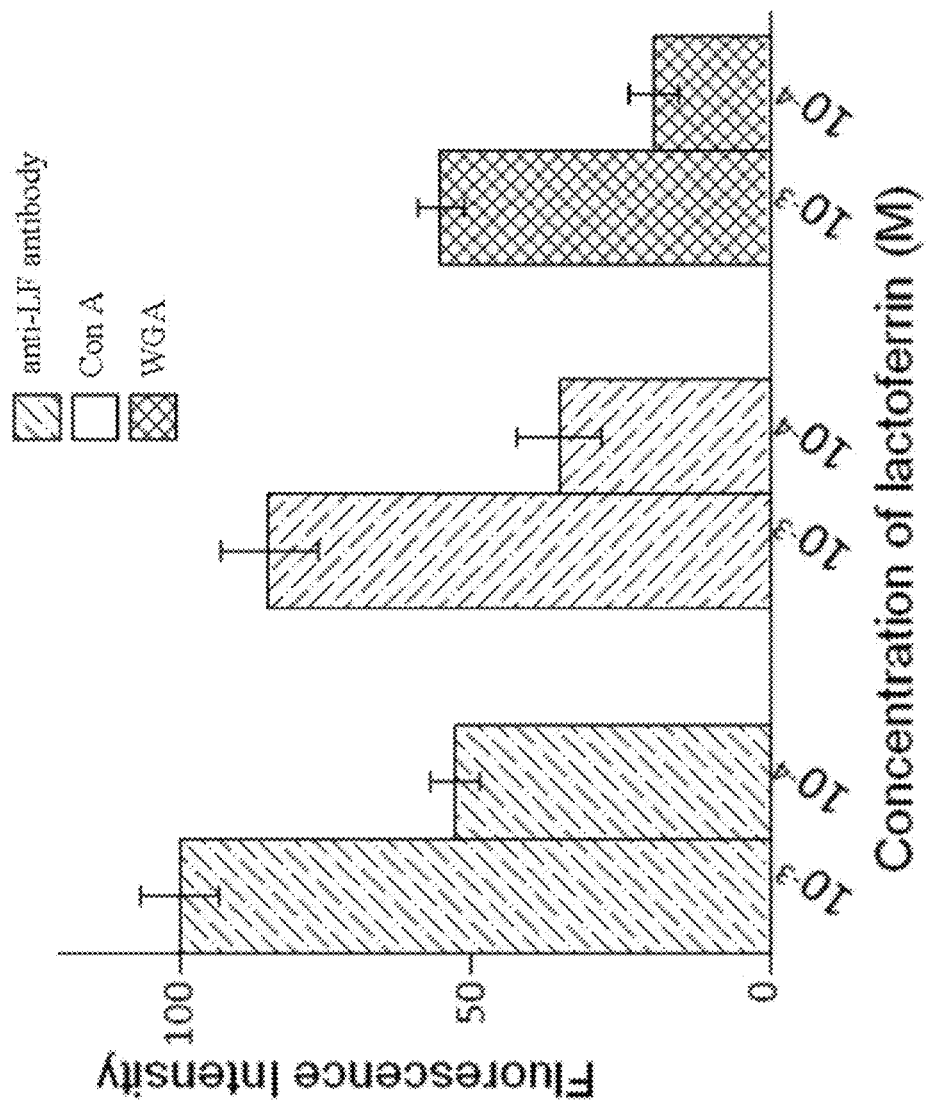
FIG. 8(a) is a quantitative analysis of fluorescence signals on microarrays with comparison of glycoprotein-protein interactions on lactoferrin microarrays (ConA-FITC-, WGA-FITC-, and FITC-labeled anti-lactoferrin antibody) according to embodiments of the present invention.
FIG. 8(b) is a quantitative analysis of fluorescence signals on microarrays with comparison of glycoprotein-protein interactions of immobilized lactoferrin, RNase B, and fetuins with FITC-labeled anti-lactoferrin antibody according to embodiments of the present invention.
Figure 8:
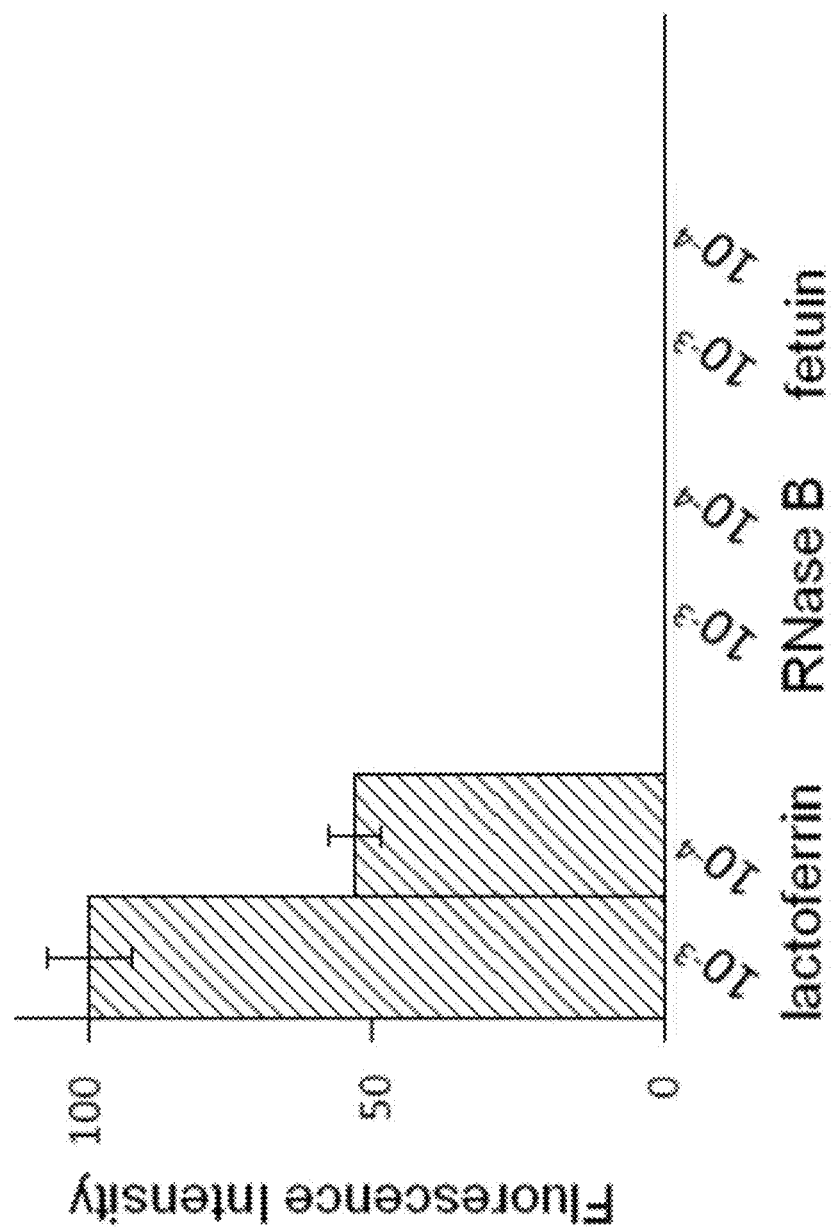

Subsequently, bovine lactoferrin, an iron-binding glycoprotein bearing five sugar chains composed of mannose, galactose, fucose, and N-acetylglucosamine, was bound to the surface of the BA-tosyl-functionalized slide. An FITC-conjugated polyclonal anti-bovine lactoferrin antibody (anti-LF antibody) was then used to examine antibody-antigen interactions after glycoprotein immobilization. A comparable intensity of anti-LF antibody/lactoferrin interaction to the carbohydrate-directed interactions with Con A-FITC and WGA-FITC was obtained and demonstrated that the traceless immobilization strategy proposed here effectively conserved the biological functions of immobilized glycoproteins for protein-protein interactions (FIG. 8(a)). The specificity of the anti-LF antibody to lactoferrin is shown in FIG. 8(b), in which RNase B and fetuins showed no binding signals with the anti-LF antibody.

In conclusion, a BA-tosyl chemical probe-directed traceless labeling strategy was developed to covalently modify glycoproteins of interest without altering the native structures of the prosthetic glycans. BA-tosyls 1-3, bearing linkers of different lengths, were synthesized and showed excellent reactivities and specificities in the successful labeling of glycosylated fetuins. Compared to the negative controls, aniline-tosyl 7 and BA-alkyne 8, there was a clear necessity for both the BA and tosyl groups in forming specific and stable covalent modifications of glycoproteins. Using BA-tosyl-functionalized glass slides, glycoprotein microarrays were prepared and successfully used in the evaluation of glycoprotein-protein interactions. The reversible conjugation of boronate diester allows the conservation of the glycan of immobilized glycoproteins and strongly supports the significance of this traceless labeling strategy in the development of glycoprotein microarrays. Compared to carbohydrate microarrays, the glycan-directed traceless glycoprotein microarray largely conserves the native structure of the glycan with the protein and, therefore, maintains its complete bioactivity, which is crucial in the evaluation of glycan-mediated protein-protein interactions. Due to their specificity in binding to glycans, the BA-tosyl-functionalized slides are believed to selectively immobilize glycoproteins from biofluids of interest without requiring prior separation or fractionation. The BA-tosyl strategy developed in this research might be a useful method for the discovery of glycoproteins and is the first strategy to provide a systematic, high-throughput microarray platform via the traceless strategy for the evaluation of glycoprotein-protein interactions.

It is necessarily supplemented that, specific processes, specific analysis methods, specific assays, specific reaction conditions, specific test glycoproteins or specific apparatuses are exemplified for clarifying the method of traceless labeling glycoproteins on the surface of the present invention and the detection kit thereto. However, as is understood by a person skilled in the art, other specific processes, other analysis methods, other assays, other reaction conditions, other test glycoproteins or other apparatuses can be also adopted in the method of traceless labeling glycoproteins on the surface of the present invention and the detection kit thereof, rather than being limited thereto.

According to the embodiments of the present invention, the aforementioned method of traceless labeling glycoproteins on the surface advantageously uses the BA-tosyl probe to bring a test glycoprotein immobilized on a surface and to expose a glycan residue of the test glycoprotein, so as to detecting the glycan residue of the test glycoprotein without altering native glycan structures, thereby being applied on a detection kit of traceless labeling glycoproteins on the surface.

Although the present invention has been described in considerable detail with reference to certain embodiments thereof, other embodiments are possible. Therefore, the spirit and scope of the appended claims should not be limited to the description of the embodiments contained herein.

What is claimed is:

1. A method of traceless labeling glycoproteins on a surface, comprising:
   providing a solid surface, wherein the solid surface has activated ester groups coated thereon;
   reacting the activated ester groups on the solid surface with an amino linker, such that a terminal amine group of the amino linker is covalently bound to a part of the activated ester groups and a terminal azide group of the amino linker is exposed, wherein the amino linker has a structure listed as formula (I):

(I) [chemical structure]

in the formula (I), the m represents an integer of 1 to 3;
   blocking an other part of the activated ester groups by a first blocking agent, wherein the other part of the activated ester groups are unreacted with the terminal amine group of the amino linker, and the first blocking agent is a glycol solution;
   reacting the terminal azide group with a tosyl group of a boric acid (BA)-tosyl probe, such that the BA-tosyl probe is immobilized on the surface via a first covalent bond and a BA moiety of the BA-tosyl probe is exposed, wherein the BA-tosyl probe has a structure listed as formula (II):

(II) [chemical structure]

in the formula (II), the $R^1$ is a boron-containing group, and an aromatic group having the $R^1$ group in the formula (II) represents a structure listed as formulas (III) to (V); the $R^2$ is a hydrogen atom, a halide atom or an alkyl group having 1 to 3 carbon numbers; the $R^3$ is a hydrogen atom or a halide atom; the $X^1$ represents $-R^4_a R^5-$, the $X^2$ represents $-R^6_p R^7_q-$, the $R^4$ has a structure listed as formula (VI), the $R^5$ has a structure listed as formula (VII), the $R^6$ has a structure listed as formula (VIII), the $R^7$ has a structure listed as formula (IX), the m represents an integer of 0 or 1, the n represents an integer of 1 to 12, and the a, p or q independently and individually represents an integer of 1;

(III) [chemical structure]

(IV) [chemical structure]

(V) [chemical structure]

(VI) [chemical structure]

(VII) [chemical structure]

(VIII) [chemical structure]

(IX) [chemical structure]

reacting the BA-tosyl probe with a test glycoprotein, such that a glycan residue of the test glycoprotein is covalently bound to the BA moiety via second covalent bond, the tosyl group is displaced with a nucleophilic residue of the test glycoprotein and released from the terminal azide group, thereby forming a first complex of the test glycoprotein and the BA-tosyl probe, wherein the first complex is immobilized on the surface via a third covalent bond;
   releasing the BA-tosyl probe from the first complex in the presence of a releasing agent, such that the glycan residue of the test glycoprotein is exposed, wherein the releasing agent is a polyol; and
   detecting the glycan residue of the test glycoprotein immobilized on the surface.

2. The method of traceless labeling glycoproteins on the surface of claim 1, wherein the activated ester groups are selected from the group consisting of an aldehyde group, a carboxyl group —O-succinimide (—O—Su) group and the combination thereof.

3. The method of traceless labeling glycoproteins on the surface of claim 1, wherein the terminal amine group of the amino linker is covalently bound to the part of the activated ester groups by an amide bond formation.

4. The method of traceless labeling glycoproteins on the surface of claim 1, wherein the glycol solution is polyol, monosaccharide or alkoxy (poly)alkylene glycol.

5. The method of traceless labeling glycoproteins on the surface of claim 4, wherein the polyol is sorbitol.

6. The method of traceless labeling glycoproteins on the surface of claim 4, wherein the monosaccharide is galactose, mannose or glucose.

7. The method of traceless labeling glycoproteins on the surface of claim 4, wherein the alkoxy (poly)alkylene glycol is selected from the group consisting of methoxy monoethylene glycol, methoxy diethylene glycol, methoxy triethylene glycol (MEG), methoxy propylene glycol, methoxy dipropylene glycol, methoxy tripropylene glycol and the combination thereof.

8. The method of traceless labeling glycoproteins on the surface of claim 1, wherein the first covalent bond is a boronate ester bond formed by covalently binding the tosyl group to the terminal azide group.

9. The method of traceless labeling glycoproteins on the surface of claim 1, wherein the second covalent bond is a cyclic boronate diester bond formed by covalently binding the tosyl group to diol groups of the glycan residue.

10. The method of traceless labeling glycoproteins on the surface of claim 1, wherein the third covalent bond is formed by the nucleophilic residue and the terminal azide group.

11. The method of traceless labeling glycoproteins on the surface of claim 1, after the step of reacting the BA-tosyl probe with the test glycoprotein, further comprising:
washing unbound test glycoprotein by a washing solution, wherein the washing solution is a glycerol solution with a concentration of 5% (v/v) to 15% (v/v).

12. The method of traceless labeling glycoproteins on the surface of claim 11, wherein the washing solution is a glycerol solution with a concentration of 7.5% (v/v) to 12.5% (v/v).

13. The method of traceless labeling glycoproteins on the surface of claim 1, wherein the polyol is selected from the group consisting of glycerin, sorbitol, mannitol and polyethylene glycol.

14. The method of traceless labeling glycoproteins on the surface of claim 1, the step of detecting the glycan residue further comprises:
contacting the glycan residue with a labeling agent, thereby forming a second complex of the test glycoprotein and the labeling agent; and
detecting an intensity generated by the labeling compound of the second complex, so as to obtain a relative amount of the glycan residue of the test glycoprotein.

15. The method of traceless labeling glycoproteins on the surface of claim 1, wherein the test glycoprotein has a concentration of 0.1 µM to 1.0 M.

16. A detection kit of traceless labeling glycoproteins on a surface, comprising:
a solid surface, wherein the solid surface has a BA-tosyl probe immobilized via a first covalent bond of an amino linker on the solid surface and a BA moiety of the BA-tosyl probe is exposed for forming a first complex of a test glycoprotein and the BA-tosyl probe via a second covalent bond, wherein the first complex is immobilized on the surface via a third covalent bond, and the BA-tosyl probe has a structure listed as formula (II):

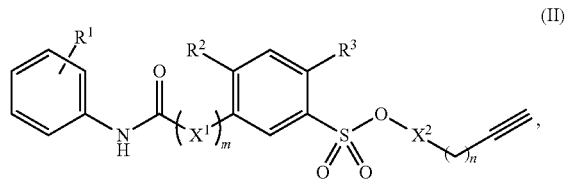

in the formula (II), the $R^1$ is a boron-containing group, and an aromatic group having the $R^1$ group in the formula (II) represents a structure listed as formulas (III) to (V); the $R^2$ is a hydrogen atom, a halide atom or an alkyl group having 1 to 3 carbon numbers; the $R^3$ is a hydrogen atom or a halide atom; the $X^1$ represents —$R^4_a R^5$—, the $X^2$ represents —$R^6_p R^7_q$—, the $R^4$ has a structure listed as formula (VI), the $R^5$ has a structure listed as formula (VII), the $R^6$ has a structure listed as formula (VIII), the $R^7$ has a structure listed as formula (IX), the m represents an integer of 0 or 1, the n represents an integer of 1 to 12, and the a, p or q independently and individually represents an integer of 1;

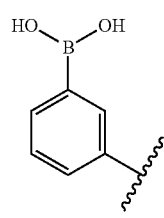

(III)

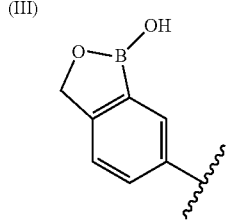

(IV)

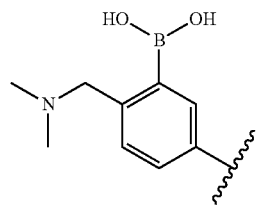

(V)

-continued

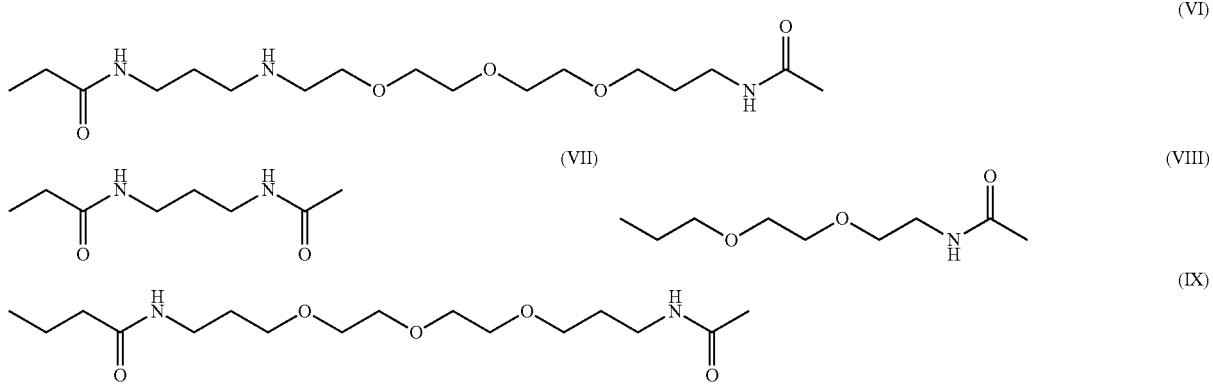

a first blocking agent for blocking other functional groups unreacted with the amino linker on the solid surface, wherein the first blocking agent is a glycol;
a releasing agent for releasing the BA-tosyl probe from the first complex, such that the glycan residue of the test glycoprotein is exposed, wherein the releasing agent is a polyol;
a washing solution for washing unbound test glycoprotein;
a labeling agent for reacting the glycan residue of the test glycoprotein, forming a second complex of the test glycoprotein and the labeling agent; and
generating a detectable intensity of the labeling compound of the second complex.

17. The detection kit of traceless labeling glycoproteins on the surface of claim 16, wherein the glycol is an alkoxy (poly)alkylene glycol selected from the group consisting of methoxy monoethylene glycol, methoxy diethylene glycol, methoxy triethylene glycol (MEG), methoxy propylene glycol, methoxy dipropylene glycol, methoxy tripropylene glycol.

18. The detection kit of traceless labeling glycoproteins on the surface of claim 16, wherein the test glycoprotein has a concentration of 0.1 μM to 1.0 M.

19. The detection kit of traceless labeling glycoproteins on the surface of claim 16, wherein the washing solution is a glycerol solution with a concentration of 5% (v/v) to 15% (v/v).

20. The detection kit of traceless labeling glycoproteins on the surface of claim 16, wherein the first covalent bond is a boronate ester bond formed by covalently binding the tosyl group to the terminal azide group.

21. The detection kit of traceless labeling glycoproteins on the surface of claim 16, wherein the second covalent bond is a cyclic boronate diester bond formed by covalently binding the tosyl group to diol groups of the glycan residue.

22. The detection kit of traceless labeling glycoproteins on the surface of claim 16, wherein the third covalent bond is formed by the nucleophilic residue and the terminal azide group.

23. The detection kit of traceless labeling glycoproteins on the surface of claim 16, wherein the polyol is selected from the group consisting of glycerin, sorbitol, mannitol and polyethylene glycol.

* * * * *